(12) United States Patent
Metcalfe et al.

(10) Patent No.: US 11,890,058 B2
(45) Date of Patent: Feb. 6, 2024

(54) ORTHOPAEDIC PLANNING SYSTEMS AND METHODS OF REPAIR

(71) Applicant: Arthrex, Inc., Naples, FL (US)

(72) Inventors: Nick Metcalfe, Bonita Springs, FL (US); Kevin John Gallen, Naples, FL (US); Ryan Megger, Chagrin Falls, OH (US)

(73) Assignee: ARTHREX, INC., Naples, FL (US)

( * ) Notice: Subject to any disclaimer, the term of this patent is extended or adjusted under 35 U.S.C. 154(b) by 274 days.

(21) Appl. No.: 17/154,395

(22) Filed: Jan. 21, 2021

(65) Prior Publication Data
US 2022/0226044 A1 Jul. 21, 2022

(51) Int. Cl.
*A61B 34/10* (2016.01)
*A61B 34/00* (2016.01)
*A61F 2/40* (2006.01)
*A61F 2/46* (2006.01)

(52) U.S. Cl.
CPC .............. *A61B 34/10* (2016.02); *A61B 34/25* (2016.02); *A61F 2/4014* (2013.01); *A61B 2034/102* (2016.02); *A61B 2034/105* (2016.02); *A61F 2002/4018* (2013.01); *A61F 2002/4633* (2013.01)

(58) Field of Classification Search
CPC ... A61B 34/10; A61B 34/25; A61B 2034/102; A61B 2034/105; A61F 2/4014; A61F 2002/4018; A61F 2002/4633
See application file for complete search history.

(56) References Cited

U.S. PATENT DOCUMENTS

| | | |
|---|---|---|
| 5,824,085 A | 10/1998 | Sahay et al. |
| 6,917,827 B2 | 7/2005 | Kienzle, III |
| 7,194,295 B2 | 3/2007 | Vilsmeier |
| 8,160,325 B2 | 4/2012 | Zug et al. |
| 8,214,016 B2 | 7/2012 | Lavallee et al. |
| 8,331,634 B2 | 12/2012 | Barth et al. |
| 8,382,765 B2 | 2/2013 | Axelson et al. |
| 8,706,197 B2 | 4/2014 | Henning et al. |
| 8,731,885 B2 | 5/2014 | Iannotti et al. |
| 9,173,665 B2 | 11/2015 | Couture |
| 9,211,199 B2 | 12/2015 | Ratron |

(Continued)

FOREIGN PATENT DOCUMENTS

| | | |
|---|---|---|
| WO | 2005089681 | 9/2005 |
| WO | 2010068212 | 6/2010 |

(Continued)

OTHER PUBLICATIONS

International Search Report and Written Opinion for International Patent Application No. PCT/US2022/012223 dated Apr. 25, 2022.

(Continued)

*Primary Examiner* — Zade Coley
*Assistant Examiner* — Diana Jones
(74) *Attorney, Agent, or Firm* — Carlson, Gaskey & Olds, P.C.

(57) ABSTRACT

This disclosure relates to planning systems and methods. The planning systems and methods disclosed herein may be utilized for planning orthopaedic procedures to restore functionality to a joint, may include determining a contact area between an implant and a cortical area of an associated bone.

30 Claims, 10 Drawing Sheets

(56) References Cited

U.S. PATENT DOCUMENTS

| | | |
|---|---|---|
| 9,299,138 B2 | 3/2016 | Zellner et al. |
| 9,498,234 B2 | 11/2016 | Goldstein et al. |
| 9,741,263 B2 | 8/2017 | Iannotti et al. |
| 10,070,928 B2 | 9/2018 | Frank et al. |
| 10,102,309 B2 | 10/2018 | McKinnon et al. |
| 10,159,530 B2 | 12/2018 | Lang |
| 10,172,675 B2 | 1/2019 | Mahfouz |
| 10,172,677 B2 | 1/2019 | Wentorf et al. |
| 10,176,642 B2 | 1/2019 | Tran et al. |
| 10,194,991 B2 | 2/2019 | Bonny et al. |
| 10,251,705 B2 | 4/2019 | Kumar et al. |
| 10,292,770 B2 | 5/2019 | Ryan et al. |
| 10,314,653 B2 | 6/2019 | Ikits et al. |
| 10,390,887 B2 | 8/2019 | Bischoff et al. |
| 10,470,821 B2 | 11/2019 | Jaramaz et al. |
| 10,537,390 B2 | 1/2020 | Varadarajan et al. |
| 10,575,875 B2 | 3/2020 | Pavlovskaia et al. |
| 10,624,655 B2 | 4/2020 | Iannotti et al. |
| 10,660,709 B2 | 5/2020 | Chaoui |
| 10,687,856 B2 | 6/2020 | Park et al. |
| 10,705,677 B2 | 7/2020 | Andersson et al. |
| 10,736,697 B2 | 8/2020 | Chaoui et al. |
| 2004/0102866 A1 | 5/2004 | Harris et al. |
| 2005/0038338 A1 | 2/2005 | Bono et al. |
| 2005/0256389 A1 | 11/2005 | Koga et al. |
| 2007/0066917 A1 | 3/2007 | Hodorek et al. |
| 2007/0179626 A1 | 8/2007 | de la Barrera et al. |
| 2007/0191741 A1 | 8/2007 | Tsai et al. |
| 2008/0033571 A1 | 2/2008 | Tuke |
| 2008/0058945 A1 | 3/2008 | Hajaj et al. |
| 2009/0089034 A1 | 4/2009 | Penney et al. |
| 2010/0030231 A1 | 2/2010 | Revie et al. |
| 2014/0324182 A1 | 10/2014 | Graumann et al. |
| 2016/0045317 A1 | 2/2016 | Lang et al. |
| 2017/0312032 A1* | 11/2017 | Amanatullah ......... G09B 23/30 |
| 2017/0367764 A1 | 12/2017 | Zuhars et al. |
| 2018/0153624 A1 | 6/2018 | Hughes et al. |
| 2018/0358120 A1 | 12/2018 | Schoenefeld et al. |
| 2018/0360544 A1 | 12/2018 | Vanheule et al. |
| 2019/0046326 A1 | 2/2019 | Ball |
| 2019/0105169 A1 | 4/2019 | Sperling |
| 2019/0175277 A1 | 6/2019 | Chav et al. |
| 2019/0231432 A1* | 8/2019 | Amanatullah ....... A61B 90/361 |
| 2019/0231433 A1* | 8/2019 | Amanatullah ..... A61B 17/1703 |
| 2019/0231434 A1* | 8/2019 | Lambers ............... A61B 34/10 |
| 2019/0336220 A1* | 11/2019 | Hladio .................. A61B 34/10 |
| 2019/0380792 A1 | 12/2019 | Poltaretskyi et al. |
| 2020/0030034 A1 | 1/2020 | Kontaxis et al. |
| 2020/0074748 A1 | 3/2020 | de Almeida Barreto et al. |
| 2020/0205898 A1 | 7/2020 | Hampp et al. |
| 2020/0205900 A1 | 7/2020 | Buckland et al. |

FOREIGN PATENT DOCUMENTS

| | | | |
|---|---|---|---|
| WO | 2010151564 | 12/2010 | |
| WO | 2017003916 | 1/2017 | |
| WO | WO-2017151863 A1 * | 9/2017 | ............. A61B 34/10 |
| WO | 2017204832 | 11/2017 | |
| WO | 2019148154 | 8/2019 | |
| WO | 2020123701 | 12/2019 | |
| WO | 2020102886 | 5/2020 | |
| WO | WO-2020123701 A1 * | 6/2020 | ............. A61B 34/10 |
| WO | 2020163328 | 8/2020 | |
| WO | 2020231654 | 11/2020 | |
| WO | WO-2020231654 A1 * | 11/2020 | ............. A61B 17/15 |

OTHER PUBLICATIONS

Brochure. Tornier Blueprint 3D Planning + PSI: Surgical Technique v.2.1—Polyamide. Wright Focused Excellence. Feb. 2017. Retrieved from: http://www.wrightmedia.com/ProductFiles/Files/PDFs/CAW-8609_EN_HR_LE.pdf.

Magosch, P., Habermeyer, P., Bachmaier, S., Metcalfe, N. (2012). Biomechanical basics of the metaphyseal anchored humeral head replacement. Springer-Verlag. 2012. pp. 1-6. (Machine translation—Google).

International Preliminary Report on Patentability for International Application No. PCT/US2022/012223 dated Aug. 3, 2023.

* cited by examiner

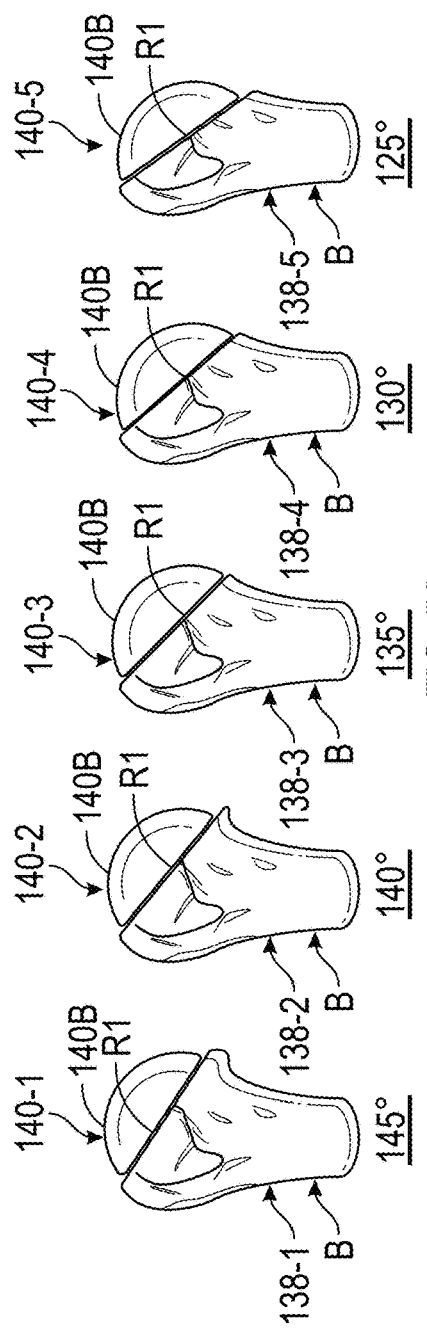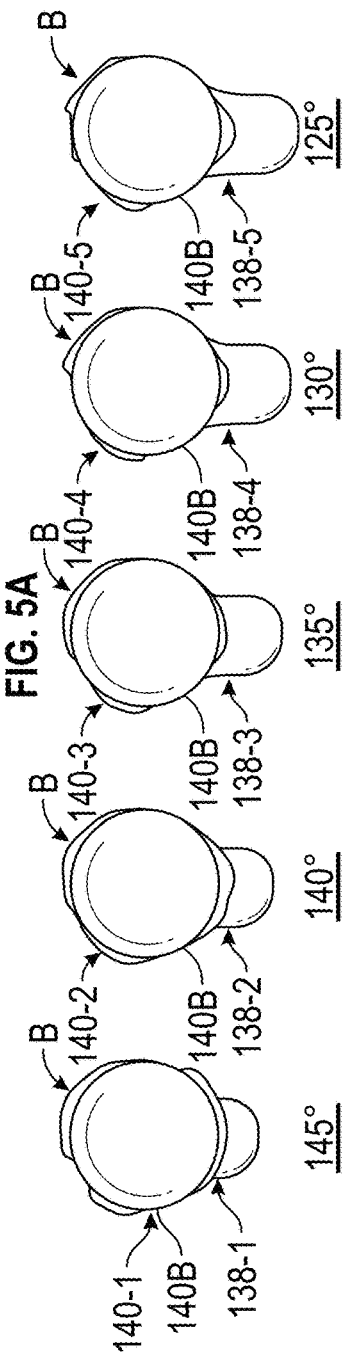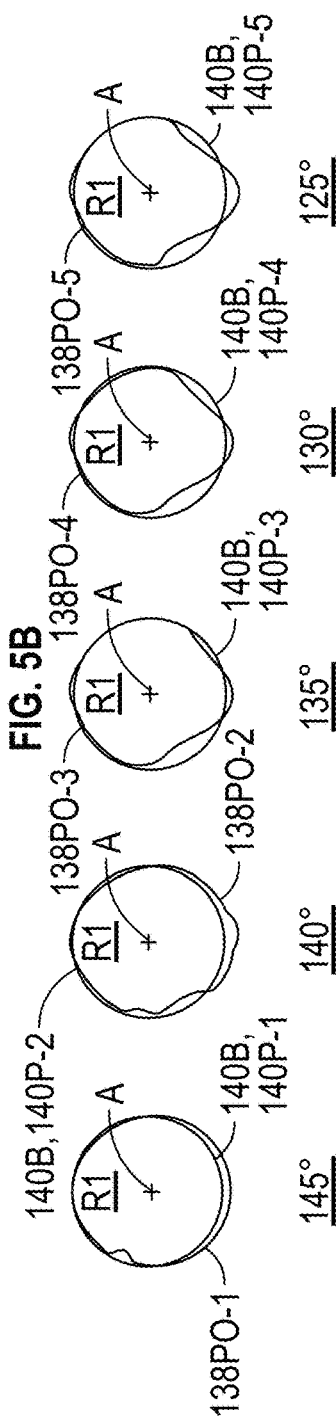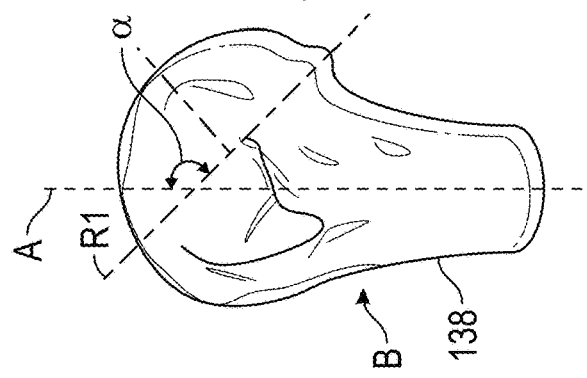

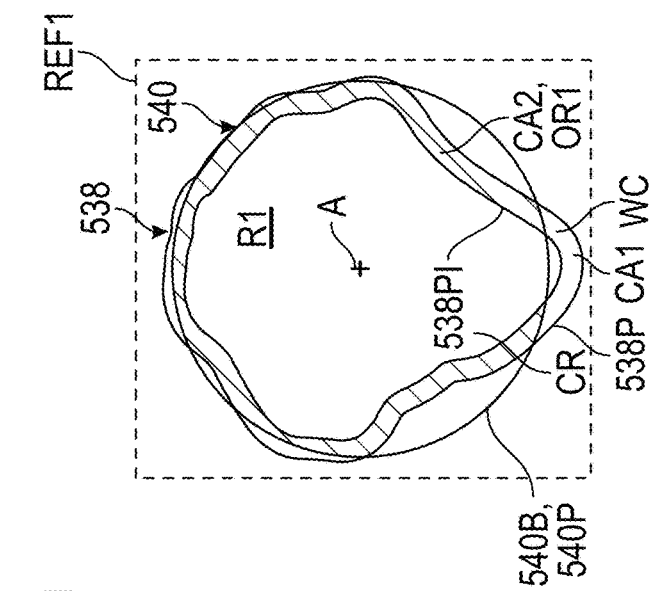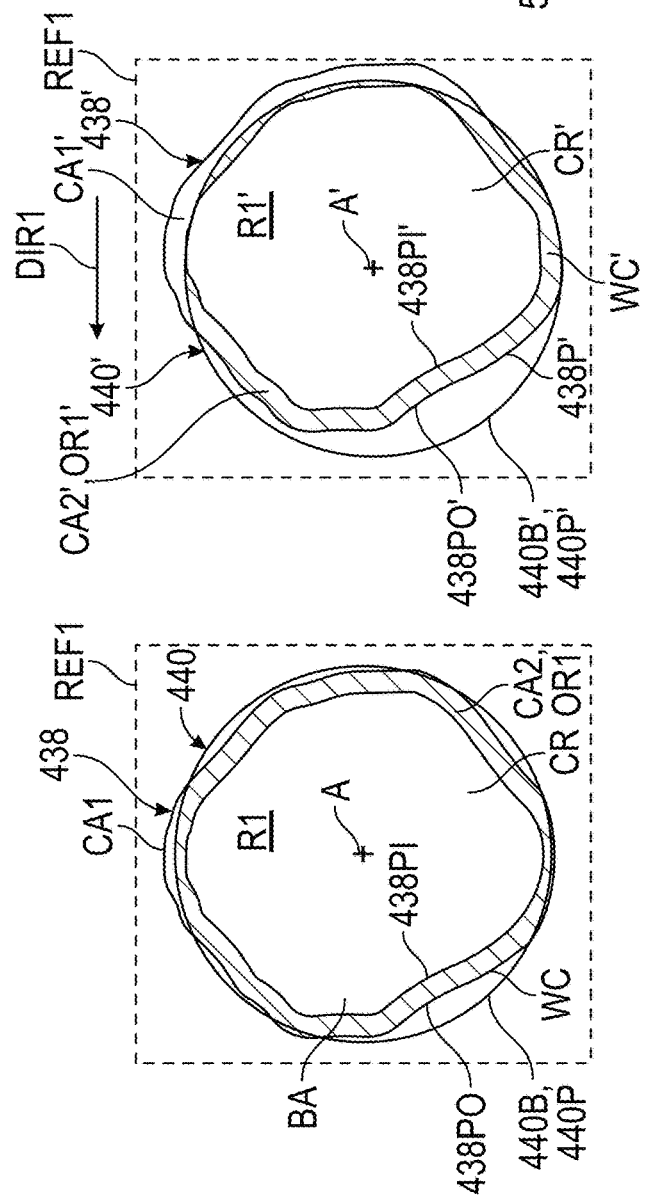

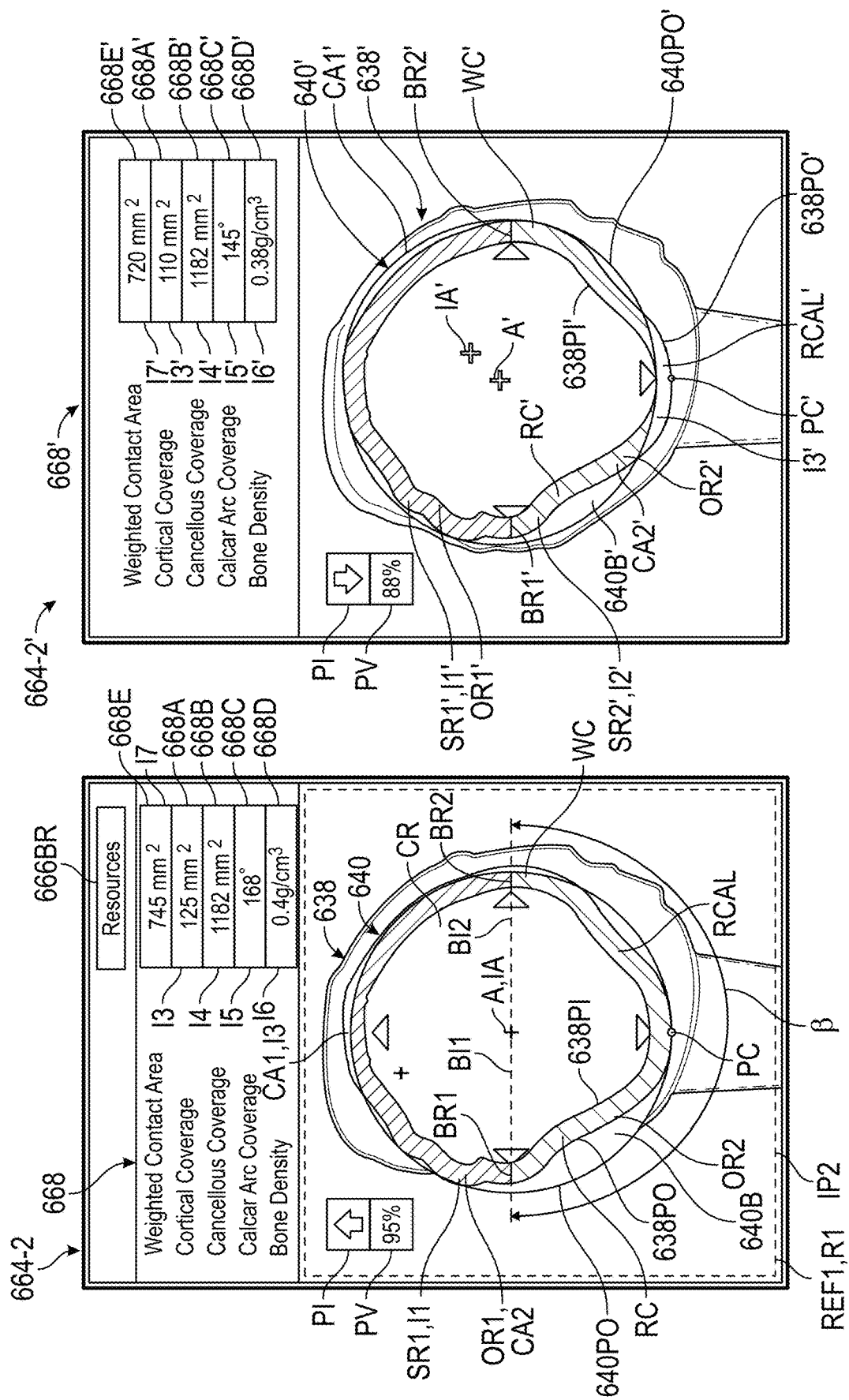

ORTHOPAEDIC PLANNING SYSTEMS AND METHODS OF REPAIR

BACKGROUND

This disclosure relates to orthopaedic procedures and, more particularly, to systems and methods for planning the repair of bone defects and restoration of functionality to a joint.

Many bones of the human musculoskeletal system include articular surfaces. The articular surfaces articulate relative to other bones to facilitate different types and degrees of joint movement. The articular surfaces can erode or experience bone loss over time due to repeated use or wear or can fracture as a result of a traumatic impact. These types of bone defects can cause joint instability and pain.

Bone deficiencies may occur along the articular surfaces. Some techniques utilize a bone graft and/or implant to repair a defect adjacent the articular surfaces.

The surgeon may establish a surgical plan relating to preparation of a surgical site, selection of an implant, and placement of the implant along the surgical site. Surgical planning may include capturing an image of the surgical site and determining a position of an implant based on the image.

SUMMARY

This disclosure relates to planning systems and methods. The planning systems may be utilized for planning orthopaedic procedures to restore functionality to a joint, including determining a contact area between an implant and a cortical area of an associated bone.

A system for planning an orthopaedic procedure of the present disclosure may include a computing device including a processor coupled to a memory. The processor may be configured to execute a planning environment including a display module, a spatial module and a comparison module. The memory may be configured to store one or more implant models and one or more bone models. The spatial module may be configured to establish an outer perimeter and an inner perimeter along a first reference plane, and the inner and outer perimeters may be associated with respective inner and outer profiles of a cortical wall of the selected bone model. The display module may be configured to display in a first display window of a graphical user interface a selected one of the implant models and a selected one of the bone models relative to a first image plane. The comparison module may be configured to determine a cortical area and a contact area. The cortical area may correspond to an area between the inner perimeter and the outer perimeter along the first reference plane. The contact area may correspond to a first region of overlap between the selected implant model and the cortical area in which the selected implant model contacts the selected bone model along the first reference plane. The comparison module may be configured to cause the display model to display at least one indicator relating to the contact area in the graphical user interface.

A method of planning an orthopaedic procedure of the present disclosure may include selecting a bone model from a plurality of bone models by interacting with a graphical user interface, selecting an implant model from a plurality of implant models by interacting with the graphical user interface, displaying in a first display window of a graphical user interface a selected one of the implant models and a selected one of the bone models relative to a first image plane, determining an outer perimeter and an inner perimeter along a first reference plane, wherein the inner and outer perimeters may be respectively associated with inner and outer profiles of a cortical wall of the selected bone model, determining a cortical area and a contact area, wherein the cortical area may correspond to an area between the inner perimeter and the outer perimeter along the first reference plane, and the contact area may correspond to a first region of overlap between the selected implant model and the cortical area in which the selected implant model contacts the selected bone model along the first reference plane, and displaying in the first display window at least one indicator relating to the contact area.

A system for planning an orthopaedic procedure of the present disclosure may include a computing device including a processor coupled to a memory. The processor may be configured to execute a planning environment including a display module, a spatial module and a comparison module. The memory may be configured to store an implant model and a bone model. The spatial module may be configured to establish a perimeter along a reference plane, and the perimeter may be associated with a profile of a cortical wall of the bone model. The display module may be configured to display in a display window of a graphical user interface the implant model and the bone model relative to an image plane. The comparison module may be configured to determine a cortical area and a contact area, the cortical area bounded by the perimeter, and the contact area may correspond to a region of overlap between the implant model and a cortical area in which the implant model contacts the bone model along the reference plane.

The various features and advantages of this disclosure will become apparent to those skilled in the art from the following detailed description. The drawings that accompany the detailed description can be briefly described as follows.

BRIEF DESCRIPTION OF THE DRAWINGS

FIG. 4 illustrates an exemplary resection angle of a bone.

FIGS. 5A-5C illustrate exemplary resections of the bone of FIG. 4 relative to different resection angles.

FIGS. 8-10 illustrate exemplary cortical areas and contact areas.

FIGS. 11-13 illustrate exemplary user interfaces displaying cortical areas and contact areas.

Like reference numbers and designations in the various drawings indicate like elements.

DETAILED DESCRIPTION

Figure 1:
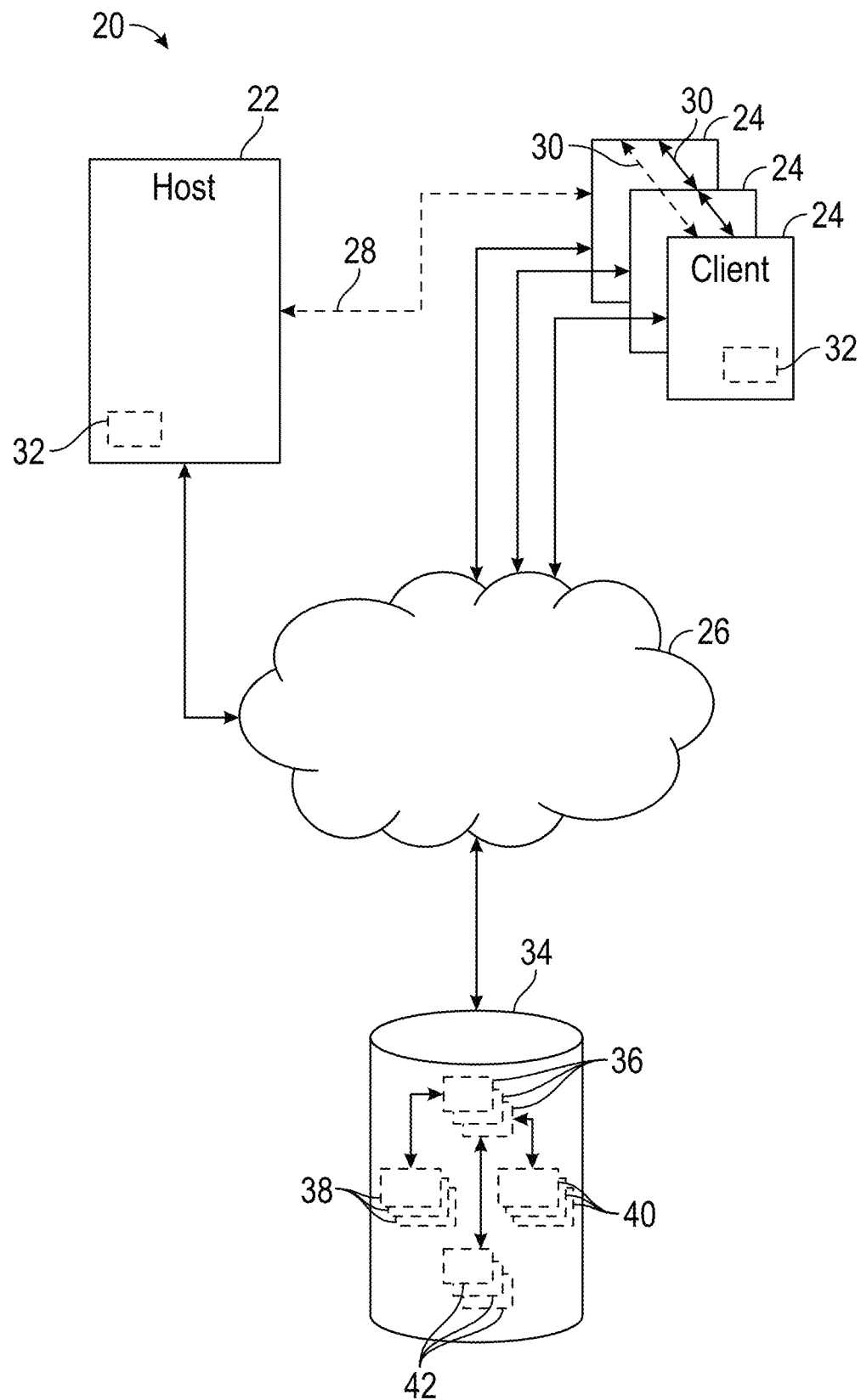
FIG. 1 illustrates an exemplary planning system.

This disclosure relates to surgical planning. The planning systems described herein may be utilized for orthopaedic procedures and may be utilized to create, edit, execute and/or review surgical plans. The surgeon may utilize the planning systems pre-operatively, intra-operatively and/or post-operatively. The planning systems and method disclosed herein may include determining a manner in which to resect a bone, and may also include determining placement of a selected implant relative the resection surface. The planning systems may determine a contact area between the implant and a cortical area of the bone along the resection surface. The planning systems may display or otherwise present the contact area in a manner that improves positioning of the implant, which may improve healing of the patient.

A system for planning an orthopaedic procedure according to an exemplary aspect of the present disclosure may include a computing device including a processor coupled to a memory. The processor may be configured to execute a planning environment including a display module, a spatial module and a comparison module. The memory may be configured to store one or more implant models and one or more bone models. The spatial module may be configured to establish an outer perimeter and an inner perimeter along a first reference plane, and the inner and outer perimeters may be associated with respective inner and outer profiles of a cortical wall of the selected bone model. The display module may be configured to display in a first display window of a graphical user interface a selected one of the implant models and a selected one of the bone models relative to a first image plane. The comparison module may be configured to determine a cortical area and a contact area. The cortical area may correspond to an area between the inner perimeter and the outer perimeter along the first reference plane. The contact area may correspond to a first region of overlap between the selected implant model and the cortical area in which the selected implant model contacts the selected bone model along the first reference plane. The comparison module may be configured to cause the display model to display at least one indicator relating to the contact area in the graphical user interface.

In some implementations, the comparison module may be configured to update the contact area in response to relative movement between the selected implant model and the selected bone model along the first reference plane.

In some implementations, the display module may be configured to set the first image plane to be parallel to the first reference plane.

In some implementations, the at least one indicator may include a visual contrast between the contact area and a remainder of the cortical area that excludes the contact area.

In some implementations, the spatial module may be configured to determine a bone area defined as an area surrounded by the outer perimeter along the first reference plane. The comparison module may be configured to determine a percentage of the contact area with respect to the bone area. The at least one indicator may be generated in response to the percentage of the contact area exceeding at least one predefined contact threshold.

In some implementations, the spatial module may be configured to establish a resection plane along the selected bone model. The resection plane may be defined by a resection angle. The display module may be configured to set the first reference plane to be coincident with the resection plane. The display module may be configured to set the first image plane to be parallel to the resection plane.

In some implementations, a volume of the selected implant model may be partially received in a volume of the selected bone model along the resection plane.

In some implementations, the comparison module may be configured to update the cortical area and the contact area in response to a change in the resection angle.

In some implementations, the graphical user interface may include a second display window. The display module may be configured to display in the second display window the selected implant model and the selected bone model relative to a second image plane. The second image plane may be transverse to the first image plane.

In some implementations, the spatial module may be configured to define a calcar region of the cortical area. The calcar region may extend through a calcar of a bone associated with the selected bone model. The comparison module may be configured to determine a second region of overlap between the calcar region and the first region of overlap. The at least one indicator may include a first indicator that identifies a portion of the first region of overlap that excludes the second region of overlap. The at least one indicator may include a second indicator that identifies the second region of overlap.

In some implementations, the first indicator and the second indicator may establish visual contrasts between each other and a remainder of the cortical area that excludes the contact area.

In some implementations, the spatial module may be configured to determine the outer perimeter in response to user interaction that defines a first set of points adjacent to the outer profile of the cortical wall. The spatial module may be configured to determine the inner perimeter in response to user interaction that defines a second set of points adjacent to the inner profile of the cortical wall.

In some implementations, the selected bone model may correspond to a bone associated with a joint.

A method of planning an orthopaedic procedure according to an exemplary aspect of the present disclosure may include selecting a bone model from a plurality of bone models by interacting with a graphical user interface, selecting an implant model from a plurality of implant models by interacting with the graphical user interface, displaying in a first display window of a graphical user interface a selected one of the implant models and a selected one of the bone models relative to a first image plane, determining an outer perimeter and an inner perimeter along a first reference plane, wherein the inner and outer perimeters may be respectively associated with inner and outer profiles of a cortical wall of the selected bone model, determining a cortical area and a contact area, wherein the cortical area may correspond to an area between the inner perimeter and the outer perimeter along the first reference plane, and the contact area may correspond to a first region of overlap between the selected implant model and the cortical area in which the selected implant model contacts the selected bone model along the first reference plane, and displaying in the first display window at least one indicator relating to the contact area.

In some implementations, the method may include updating the contact area in response to moving the selected implant model relative to the selected bone model.

In some implementations, the method may include selecting a resection angle to define a resection plane along the selected bone model. The method may include setting the first reference plane to be coincident with the resection plane. The method may include setting the first image plane to be parallel to the resection plane.

In some implementations, the method may include displaying in a second display window of the graphical user interface the selected implant model and the selected bone model relative to a second image plane. The second image plane may be transverse to the first image plane.

In some implementations, the method may include setting the second image plane to be perpendicular to the first image plane. The method may include positioning the selected implant model along the resection plane such that a volume of the selected implant model may be partially received in a volume of the selected bone model.

In some implementations, the method may include updating the determined cortical area and the determined contact area in response to changing the selected resection angle.

In some implementations, the method may include determining a bone area, wherein the bone area is defined as an area surrounded by the outer perimeter along the first reference plane. The method may include determining a percentage of the contact area with respect to the bone area. The method may include displaying the percentage of the contact area in the graphical user interface. The at least one indicator may include a first indicator and a second indicator. The method may include displaying the first indicator in response to the percentage of the contact area meeting at least one predefined contact threshold, but displaying the second indicator in response to the percentage of the contact area being below the at least one predefined contact threshold.

In some implementations, the method may include determining a second region of overlap between the contact area and a calcar region of the cortical area. The calcar region may extend through a calcar of a bone associated with the selected bone model. The method may include displaying a perimeter of the second region of overlap in the first display window. The method may include displaying a perimeter of a remainder of the contact area in the first display window that excludes the second region of overlap. The method may include displaying a perimeter of a remainder of the cortical area in the first display window that excludes the contact area.

In some implementations, the at least one indicator may include a first indicator and a second indicator. The method may include determining a cancellous area of the selected bone model. The cancellous area may correspond to an area along the first reference plane that is surrounded by the inner perimeter. The first region of overlap may be associated with a first weight, the second region of overlap may be associated with a second weight, the cancellous area may be associated with a third weight, and the first weight may be greater than the third weight but may be less than the second weight. The method may include determining a weighted value of the contact area according to the first, second and third weights. The method may include displaying the first indicator in the graphical user interface in response to the weighted contact area exceeding at least one predefined weighted contact threshold, but displaying the second indicator in the graphical user interface in response to the weighted contact area being below the at least one predefined weighted contact threshold.

In some implementations, the at least one indicator may include a third indicator and a fourth indicator. The method may include determining a bone density of the selected bone model along the contact area based on the weighted value of the contact area. The method may include displaying the third indicator in the graphical user interface in response to the bone density exceeding at least one predefined density threshold, but displaying the fourth indicator in the graphical user interface in response to the bone density being below the at least one predefined density threshold.

In some implementations, the method may include selecting a resection angle to define a resection plane along the selected bone model. The method may include setting the first reference plane to be coincident with the resection plane. The method may include setting the first image plane to be parallel to the resection plane. The method may include performing at least one of the following steps in response to the weighted contact area being below the at least one predefined weighted contact threshold: selecting another implant model from the plurality of implant models; changing the selected resection angle; moving the selected implant model along the resection plane; and/or rotating the selected implant model about an implant axis that extends through the resection plane.

In some implementations, the selected bone model may correspond to a bone associated with a joint.

In some implementations, the bone may be a humeral head of a humerus.

A system for planning an orthopaedic procedure according to an exemplary aspect of the present disclosure may include a computing device including a processor coupled to a memory. The processor may be configured to execute a planning environment including a display module, a spatial module and a comparison module. The memory may be configured to store an implant model and a bone model. The spatial module may be configured to establish a perimeter along a reference plane, and the perimeter may be associated with a profile of a cortical wall of the bone model. The display module may be configured to display in a display window of a graphical user interface the implant model and the bone model relative to an image plane. The comparison module may be configured to determine a cortical area and a contact area, the cortical area bounded by the perimeter, and the contact area may correspond to a region of overlap between the implant model and a cortical area in which the implant model contacts the bone model along the reference plane.

In some implementations, the comparison module may be configured to cause the display model to display an indicator relating to the contact area in the graphical user interface.

FIG. 1 illustrates an exemplary planning system 20 that may be utilized for planning surgical procedures. The system 20 may be used for planning orthopaedic procedures, including pre-operatively, intra-operatively and/or post-operatively to create, edit, execute and/or review surgical plans.

The system 20 may include a host computer 22 and one or more client computers 24. The host computer 22 may be configured to execute one or more software programs. In some implementations, the host computer 22 is more than one computer jointly configured to process software instructions serially or in parallel.

The host computer 22 may be in communication with one or more networks such as a network 26 comprised of one or more computing devices. The network 26 may be a private local area network (LAN), a private wide area network (WAN), the Internet, or a mesh network, for example.

The host computer 22 and each client computer 24 may include one or more of a computer processor, memory, storage means, network device and input and/or output devices and/or interfaces. The input devices may include a keyboard, mouse, etc. The output device may include a monitor, speakers, printers, etc. The memory may, for example, include UVPROM, EEPROM, FLASH, RAM, ROM, DVD, CD, a hard drive, or other computer readable medium which may store data and/or other information relating to the planning techniques disclosed herein. The host computer 22 and each client computer 24 may be a desktop computer, laptop computer, smart phone, tablet, or any other computing device. The interface may facilitate communication with the other systems and/or components of the network 26.

Each client computer 24 may be configured to communicate with the host computer 22 directly via a direct client interface 28 or over the network 26. The client computers 24 may be configured to execute one or more software programs, such as a various surgical tools. The planning package may be configured to communicate with the host computer 22 either over the network 26 or directly through the direct client interface 28. In another implementation, the client computers 24 are configured to communicate with each other directly via a peer-to-peer interface 30.

Each client computer 24 may be operable to access and locally and/or remotely execute a planning environment 32. The planning environment 32 may be a standalone software package or may be incorporated into another surgical tool. The planning environment 32 may provide a display or visualization of one or more bone models and related images and one or more implant models via one or more graphical user interfaces (GUI). Each bone model, implant model, and related images and other information may be stored in one or more files or records according to a specified data structure.

The system 20 may include at least one storage system 34, which may be operable to store or otherwise provide data to other computing devices. The storage system 34 may be a storage area network device (SAN) configured to communicate with the host computer 22 and/or the client computers 24 over the network 26, for example. In implementations, the storage system 34 may be incorporated within or directly coupled to the host computer 22 and/or client computers 24. The storage system 34 may be configured to store one or more of computer software instructions, data, database files, configuration information, etc.

In some implementations, the system 20 is a client-server architecture configured to execute computer software on the host computer 22, which is accessible by the client computers 24 using either a thin client application or a web browser executing on the client computers 24. The host computer 22 may load the computer software instructions from local storage, or from the storage system 34, into memory and may execute the computer software using the one or more computer processors.

The system 20 may include one or more databases 36. The databases 36 may be stored at a central location, such as the storage system 34. In another implementation, one or more databases 36 may be stored at the host computer 22 and/or may be a distributed database provided by one or more of the client computers 24. Each database 36 may be a relational database configured to associate one or more bone models 38 and one or more implant models 40 to each other and/or a surgical plan 42. Each surgical plan 42 may be associated with a respective patient. Each bone model 38, implant model 40 and surgical plan 42 may be assigned a unique identifier or database entry. The database 36 may be configured to store data corresponding to the bone models 38, implant models 40 and surgical plans 42 in one or more database records or entries, and/or may be configured to link or otherwise associate one or more files corresponding to each respective bone model 38, implant model 40 and surgical plan 42. Bone models 38 stored in the database(s) 36 may correspond to respective patient anatomies from prior surgical cases, and may be arranged into one or more predefined categories such as sex, age, ethnicity, defect category, procedure type, etc.

Each bone model 38 may include information obtained from one or more medical devices or tools, such as a computerized tomography (CT), magnetic resonance imaging (MRI) machine and/or X-ray machine, that obtains one or more images of a patient. The bone model 38 may include one or more digital images and/or coordinate information relating to an anatomy of the patient obtained or derived from the medical device(s). Each implant model 40 may include coordinate information associated with a predefined design. The planning environment 32 may incorporate and/or interface with one or more modeling packages, such as a computer aided design (CAD) package, to render the models 38, 40 as two-dimensional (2D) and/or three-dimensional (3D) volumes or constructs.

The predefined design may correspond to one or more components. The implant models 40 may correspond to implants and components of various shapes and sizes. Each implant may include one or more components that may be situated at a surgical site including screws, anchors and/or grafts. Each implant model 40 may correspond to a single component or may include two or more components that may be configured to establish an assembly. Each bone model 38 and implant model 40 may correspond to 2D and/or 3D geometry, and may be utilized to utilized to generate a wireframe, mesh and/or solid construct in a display.

Each surgical plan 42 may be associated with one or more of the bone models 38 and implant models 40. The surgical plan 42 may include one or more revisions to bone model 38 and information relating to a position of an implant model 40 relative to the original and/or revised bone model 38. The surgical plan 42 may include coordinate information relating to the revised bone model and a relative position of the implant model 40 in predefined data structure(s). Revisions to each bone model 38 and surgical plan 42 may be stored in the database 36 automatically and/or in response to user interaction with the system 20.

One or more surgeons and other users may be provided with a planning environment 32 via the client computers 24 and may simultaneously access each bone model 38, implant model 40 and surgical plan 42 stored in the database(s) 36. Each user may interact with the planning environment 32 to create, view and/or modify various aspects of the surgical plan 42. Each client computer 24 may be configured to store local instances of the bone models 38, implant models 40 and/or surgical plans 42, which may be synchronized in real-time or periodically with the database(s) 36. The planning environment 32 may be a standalone software package executed on a client computer 24 or may be provided as one or more services executed on the host computer 22, for example.

Figure 2:
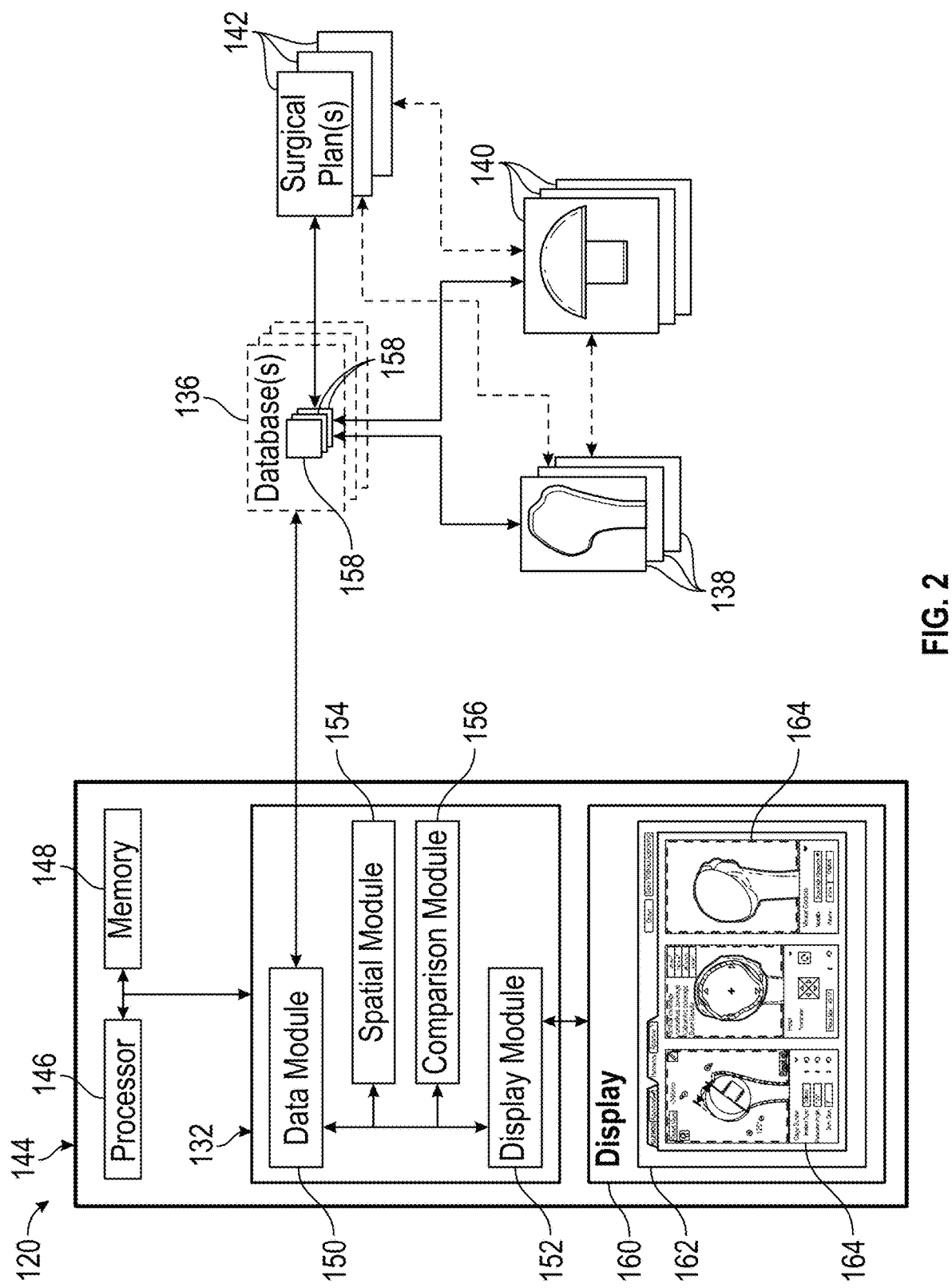
FIG. 2 illustrates another exemplary planning system including a user interface.

FIG. 2 illustrates an exemplary planning system 120 for planning a surgical procedure. The system 120 may be utilized for various orthopaedic and other surgical procedures, such as an arthroplasty to repair a joint. The system 120 may be utilized in the placement of an implant, such as an implant incorporated into a shoulder prosthesis, for example. Although the planning systems and methods disclosed herein primarily refer to repair of a humerus during an anatomic or reverse shoulder reconstruction, it should be understood that the planning system 120 may be utilized in the repair of other locations of the patient and other surgical procedures including repair of a glenoid and other joints such as a wrist, hand, hip, knee or ankle, and including repair of fractures.

The system 120 may include a computing device 144 including at least one processor 146 coupled to memory 148. The computing device 144 can include any of the computing devices disclosed herein, including the host computer 22 and/or client computer 24 of FIG. 1. The processor 146 may be configured to execute a planning environment 132 for creating, editing, executing and/or reviewing one or more surgical plans 142 during pre-operative, intra-operative and/or post-operative phases of a surgery.

The planning environment 132 may include at least a data module 150, a display module 152, a spatial module 154 and a comparison module 156. Although four modules are shown, it should be understood that fewer or more than four modules may be utilized and/or one or more of the modules may be combined to provide the disclosed functionality.

The data module 150 may be configured to access, retrieve and/or store data and other information in the database(s) 136 corresponding to one or more bone model(s) 138, implant model(s) 140 and/or surgical plan(s) 142. The data and other information may be stored in one or more databases 136 as one or more records or entries 158. In some implementations, the data and other information may be stored in one or more files that are accessible by referencing one or more objects or memory locations references by the records or entries 158.

The memory 148 may be configured to access, load, edit and/or store instances of one or more bone models 138, implant models 140 and/or surgical plans 142 in response to one or more commands from the data module 150. The data module 150 may be configured to cause the memory 148 to store a local instance of the bone model(s) 138, implant model(s) 140 and/or surgical plan(s) 142 which may be synchronized with records 158 in the database(s) 136.

The display module 152 may be configured to display data and other information relating to one or more surgical plans 142 in at least one graphical user interface (GUI) 162. The computing device 144 may be coupled to a display device 160. The display module 152 may be configured to cause the display device 160 to display information in the user interface 162. A surgeon or other user may interact with the user interface 162 via the planning environment 132 to create, edit, execute and/or review one or more surgical plans 142.

Figure 3:
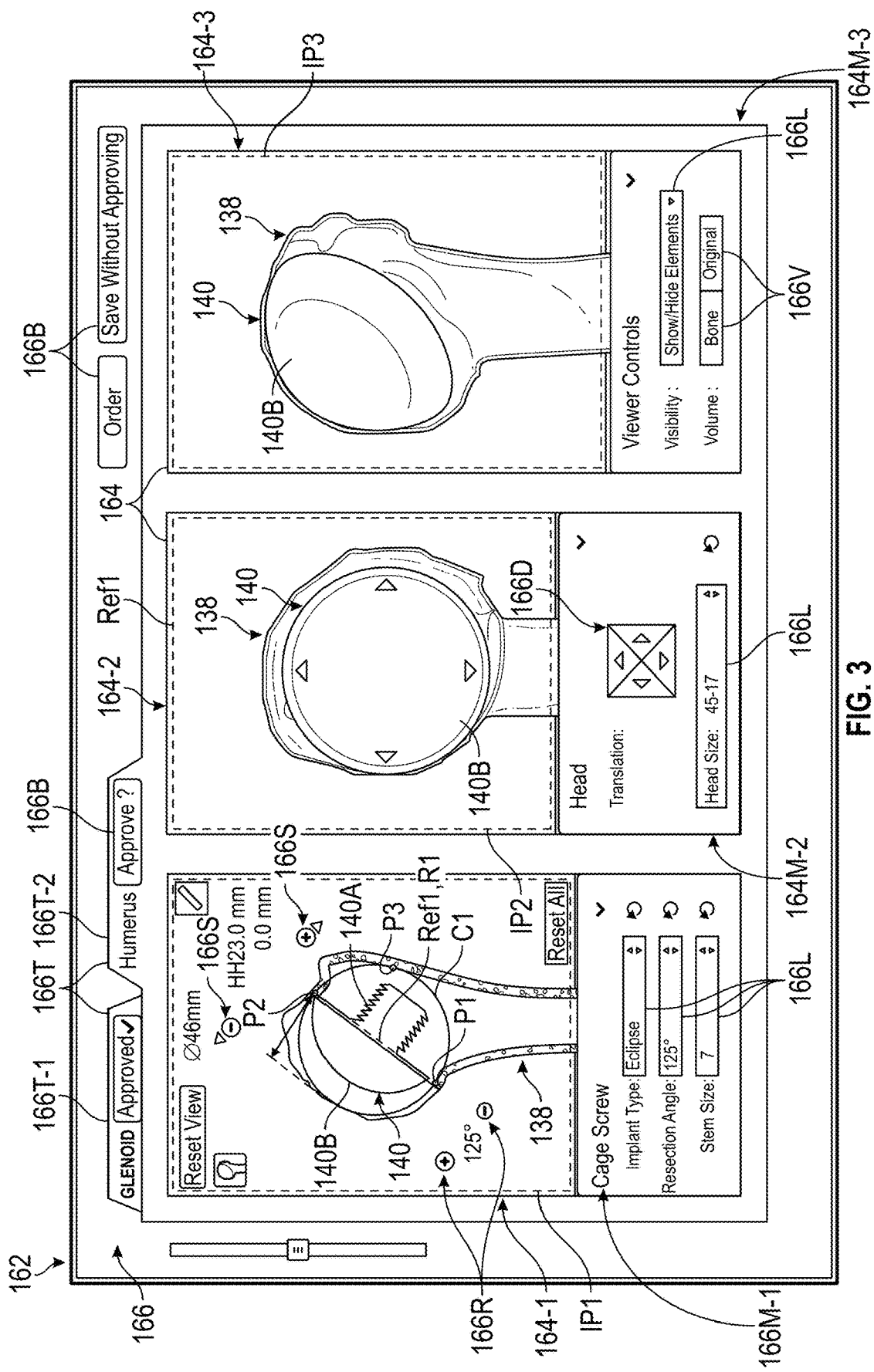
FIG. 3 illustrates the user interface of FIG. 2.

Referring to FIG. 3, with continuing reference to FIG. 2, the user interface 162 may include one or more display windows 164 and one or more objects 166. The objects 166 may include graphics such as menus, tabs and buttons accessible by user interaction, such as tabs 166T, buttons 166B, 166R, 166S, 166V, drop-down lists 166L, and directional indicator 166D. Geometric objects including selected bone model(s) 138 and implant model(s) 140 and other information relating to the surgical plan 142 may be displayed in one or more of the display windows 164.

The implant model 140 may include one or more components. For example, the implant model 140 may include at least a first component 140A and a second component 140B coupled to the first component 140A to establish an assembly. The first component 140A may be configured to be at least partially received in a volume of a selected one of the bone models 138. The second component 140B may have an articulation surface dimensioned to mate with an articular surface of an opposed bone or implant.

The display windows 164 may include first, second and third display windows 164-1, 164-2, 164-3. Although three display windows 164 are illustrated in FIG. 3, it should be understood that fewer or more than three display windows 164 can be utilized in accordance with the teachings disclosed herein.

The first, second and third display windows 164-1, 164-2, 164-3 may be associated with respective first, second and third image planes IP1, IP2, IP3 (shown in dashed lines for illustrative purposes). The first, second and/or third image planes IP1, IP2, IP3 may be substantially perpendicular or otherwise transverse to each other.

The display module 152 may be configured to display in the first, second and third display windows 164-1, 164-2, 164-3 a selected one of the one or more bone models 138 and a selected one of the one or more implant models 140 relative to the respective image planes IP1, IP2, IP3. The display module 152 may be configured such that the selected bone model 138 and/or selected implant model 140 may be selectively displayed and hidden (e.g., toggled) in one or more of the display windows 164 in response to user interaction with the user interface 162, which may provide the surgeon with enhanced flexibility in reviewing aspects of the surgical plan 142.

The display module 152 may be configured to display 2D representation(s) of the selected bone model 138 and/or selected implant model 140 in the first and/or second display windows 164-1, 164-2. The surgeon may interact with the respective display windows 164-1, 164-2 or another portion of the user interface 162 to move the selected bone model 138 and/or selected implant model 140 in 2D space (e.g., up, down, left, right). The image planes P1 and/or P2 may be locked to a single respective 2D perspective, as illustrated in FIG. 3. In other implementations, the display module 152 may be configured to display 3D representation(s) of the selected bone model 138 and/or selected implant model 140 in the first and/or second display windows 164-1, 164-2.

The selected bone model 138 may correspond to a bone associated with a joint, such as a humerus as illustrated in FIG. 3. The display module 152 may be configured to display a sectional view of the selected bone model 138 and/or selected implant model 140 in the first viewing window 164-1. The sectional view may be presented as an image of the bone associated with the selected bone model 138. The display module 152 may be configured to set the first image plane IP1 to be parallel to the sectional view. An orientation of the sectional view may be predefined or may be specified in response to user interaction with the user interface 162.

The spatial module 154 may be configured to establish a resection plane R1 along the selected bone model 138 (R1 shown in dashed lines in window 164-1 for illustrative purposes). A volume of the selected implant model 140 may be at least partially received in a volume of the selected bone model 138 along the resection plane RE The resection plane R1 may be defined by a resection angle α, as illustrated in FIG. 4. The resection angle α may be defined with respect to an angle between the resection plane R1 and a longitudinal axis A of a bone B associated with the selected bone model 138. The spatial module 154 may be configured to cause the display module 152 to display an excised portion of the selected bone model 138 to be displayed in the first display window 164-1 in a different manner than a remainder of the bone model 138 on an opposed side of the resection plane R1, such as a relatively darker shade as illustrated by the humeral head in FIG. 3. In other implementations, the excised portion may be hidden from display in the first display window 164-1. The spatial module 154 may determine the excised portion by comparing coordinates of the bone model 138 with respect to a position of the resection plane R1, for example.

The display module 152 may be configured to set the second image plane IP2 of the second display window 164-2 to be parallel to a first reference plane REF1. The display module 152 may be configured to set the first reference plane REF1 to be coincident with the resection plane RE Arranging the second display window 164-2 such that a viewpoint of the surgeon is substantially normal to the resection plane R1 may provide improved visualization and positioning of the selected implant model 140 relative to a resected surface of the selected bone model 138.

The user interface 162 may arranged in one or more tabs 166T. The surgeon may interact with each of the tabs 166T to specify various aspects of a surgical plan 142. For example, the surgeon may select a first tab 166T-1 to view or specify aspects of the surgical plan 142 for one portion of a joint, such as a glenoid, and may select a second tab 166T-2 to view or specify aspects of the surgical plan 142 for another portion of the joint, such as a humerus, as illustrated in FIG. 3.

The user may interact with a first set of menu items 166M-1 associated with the first display window 164-1 to select and specific various aspects of an implant model 140 from the database 136 (FIG. 2). For example, the user may interact with the drop-down lists 166L in the first set of menu items 166M-1 to specify implant type, resection angle and implant size. The resection angle menu item may be associated with the resection plane R1, which may be displayed as being substantially perpendicular to the first image plane IP1.

The user may interact with a set of buttons 166R to change (e.g., increase or decrease) the resection angle. The user may interact with a set of buttons 166S adjacent the selected implant model 140 to change (e.g., increase or decrease) a size of a component of the selected implant model 140. The sets of buttons 166R, 166S may be overlaid onto the first display window 164-1.

The surgeon may interact with a second set of menu items 166M-2 associated with the second display window 164-2 to specific various aspects of the selected implant model 140. For example, the user may interact with the directional indicator 166D to move a portion of the selected implant model 140 in different directions (e.g., up, down, left, right) relative to the second image plane IP2. In some implementations, the surgeon may drag the selected implant model 140 to a desired position in the second display window 164-2 utilizing a mouse, and may utilize the directional indicator 166D to more finely tune the position of the selected implant model 140. The surgeon may interact with one or more drop-down lists 166L in the second list of menu items 166M-2 to specify a type and/or size of a component of the selected implant model 140.

The display module 152 may be configured to display a 3D representation of the selected bone model 138 and/or selected implant model 140 in the third display window 164-3. The surgeon may interact with the third display window 164-3 or another portion of the user interface 162 to move the selected bone model 138 and/or selected implant model 140 in 3D space. In other implementations, the display module 152 may be configured to display a 2D representation of the selected bone model 138 and/or selected implant model 140 in the third display window 164-3.

The surgeon may interact with a third set of menu items 166M-3 associated with the third display window 164-3 to specific various aspects of the selected bone model 138 and/or selected implant model 140. For example, the surgeon may interact with one or more drop-down lists 166L in the third set of menu items 166M-3 to selectively display and hide components of the selected implant model 140. The user may interact with one or more buttons 166V in the third list of menu items 166M-3 to toggle between a volume of previous and revised (e.g., resected) states of the selected bone model 138.

The planning environment 132 may be configured such that changes in one of the display windows 164 are synchronized with each of the other windows 164. The changes may be synchronized between the display windows 164 automatically and/or manually in response to user interaction.

The surgeon may interact with the user interface 162 to evaluate implant placement relative to different resection angles for a selected bone model 138. FIGS. 5A-5C illustrate exemplary resections of the bone B of FIG. 4 relative to different resection angles. Each resection angle is illustrated by a respective bone model 138-1 to 138-5, which may correspond to the same bone B. Bone models 138-1 to 138-5 may be associated with respective resection angles of 145, 140, 135, 130 and 125 degrees and a corresponding resection plane R1, for example. FIG. 5A may correspond to a side view of the respective bone models 138-1 to 138-5. FIG. 5B may correspond to a view of the respective bone models 138-1 to 138-5 parallel to the respective resection planes R1 (see FIGS. 5A and 5C). FIG. 5C may correspond to a view of the respective bone models 138-1 to 138-5 parallel to the respective resection planes R1, with outer perimeters 138PO-1 to 138PO-5 of the respective bone models 138-1 to 138-5 and perimeters 140P-1 to 140P-5 of the respective implant models 140 shown. It should be understood that the arrangements of FIGS. 5A-5C are exemplary and other arrangements may be utilized in accordance with the teachings disclosed herein. As illustrated by FIGS. 4 and 5C, a contour of the bone B associated with the bone model 138 may vary along a length and circumference of the bone B and may therefore have different surface areas and perimeter geometries along the respective resection plane R1.

Figure 6B:
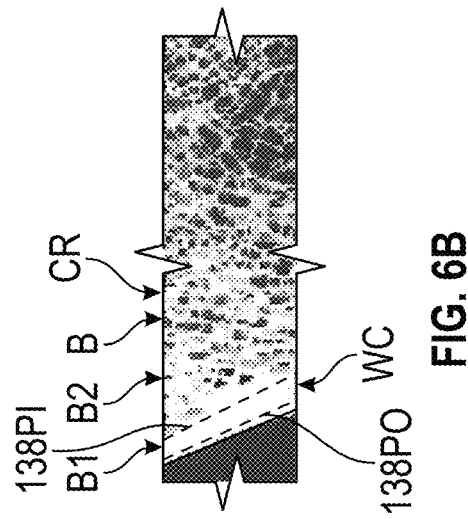
FIGS. 6A-6B illustrate a bone model and an associated bone resected along a resection plane.
Figure 6A:
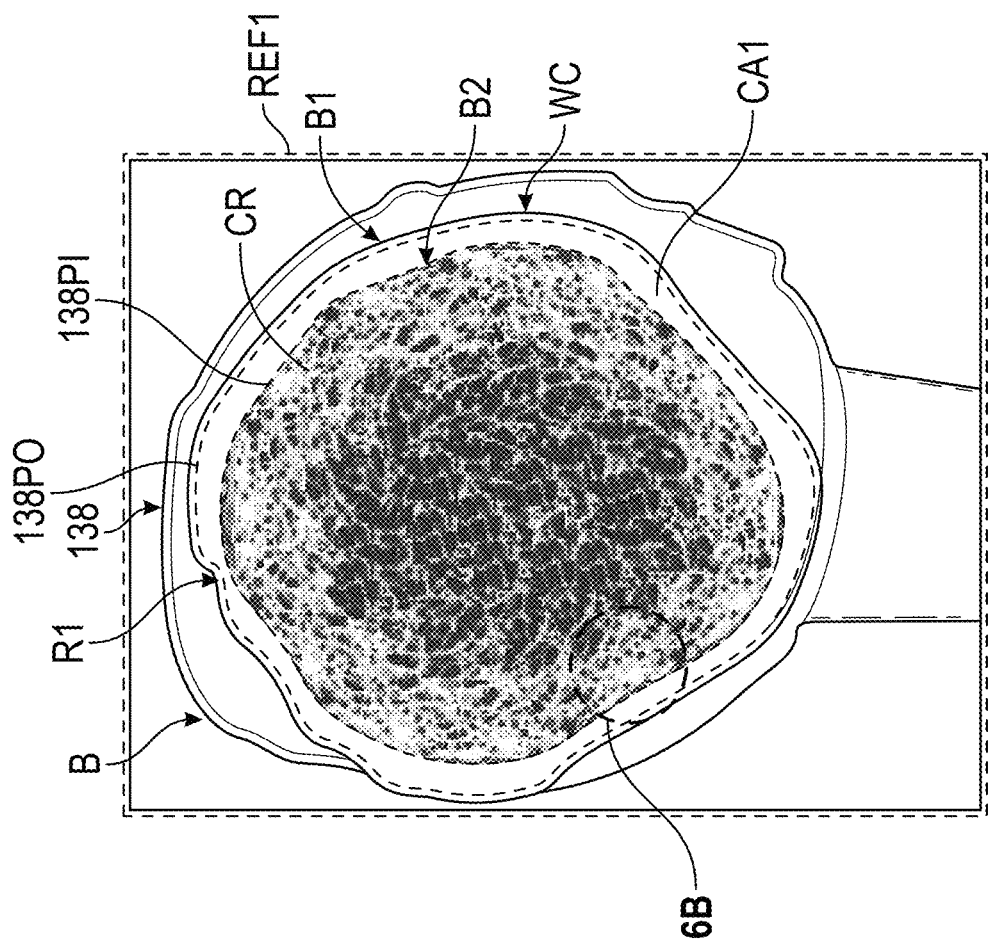

FIG. 6A illustrates an exemplary bone B resected along a resection plane R1 and aspects of the bone model 138. Resection of the bone B along the resection plane R1 exposes cortical bone B1 and cancellous bone B2. The cortical bone B1 may comprise substantially hard and dense bone tissue, whereas the cancellous bone B2 may comprise relatively porous, spongy bone tissue, as illustrated in FIG. 6B. The cortical bone B1 may establish a cortical wall WC that surrounds the cancellous bone B2.

The spatial module 154 may be configured to establish or determine at least one perimeter of a bone B associated with the respective bone model 138, such as an inner perimeter 138PI and/or outer perimeter 138PO. The spatial module 154 may be configured to establish or determine the inner perimeter 138PI and/or outer perimeter 138PO along a first reference plane REF1 (shown in dashed lines for illustrative purposes). The first reference plane REF1 may correspond to the resection plane R1 (FIG. 3). The inner perimeter 138PI and outer perimeter 138PO may be associated with respective inner and outer profiles of the cortical wall WC a bone associated with the selected bone model 138. The cortical wall WC may correspond to or substantially approximate a cortical wall established by cortical bone tissue C1 of the bone B. The cortical wall WC may surround a cancellous region CR. The cancellous region CR may correspond to or substantially approximate a region established by cancellous bone tissue C2 of the bone B.

Various techniques may be utilized to determine at least one perimeter associated with a profile of the cortical wall WC of a bone B and the respective bone model 138, such as the inner perimeter 138PI and/or outer perimeter 138PO. The spatial module 154 may be configured to establish at least one perimeter along the reference plane REF1, including the inner perimeter 138PI and/or outer perimeter 138PO, to establish a cortical area CA1. The cortical area CA1 may correspond to an area between the inner perimeter 138PI and outer perimeter 138PO along the first reference plane REF1.

In some implementations, the spatial module 154 may be configured to execute one or more edge detection algorithms to determine the inner perimeter 138PI and/or outer perimeter 138PO that respectively approximate inner and outer boundaries of the cortical wall WC. Edge detection algorithms are known, and generally determine one or more edges in a digital image based gradients established between adjacent pixels in the image. However, utilizing edge detection techniques in accordance with the teachings disclosed herein is not known. The spatial module 154 may be configured to determine the inner and outer boundaries of the cortical wall WC based on gradients established by the cortical bone B1 and cancellous bone B2 in the respective image, as illustrated by FIG. 6A. One would understand how to program the spatial module 154 to execute various edge detection algorithms.

Figure 7A:
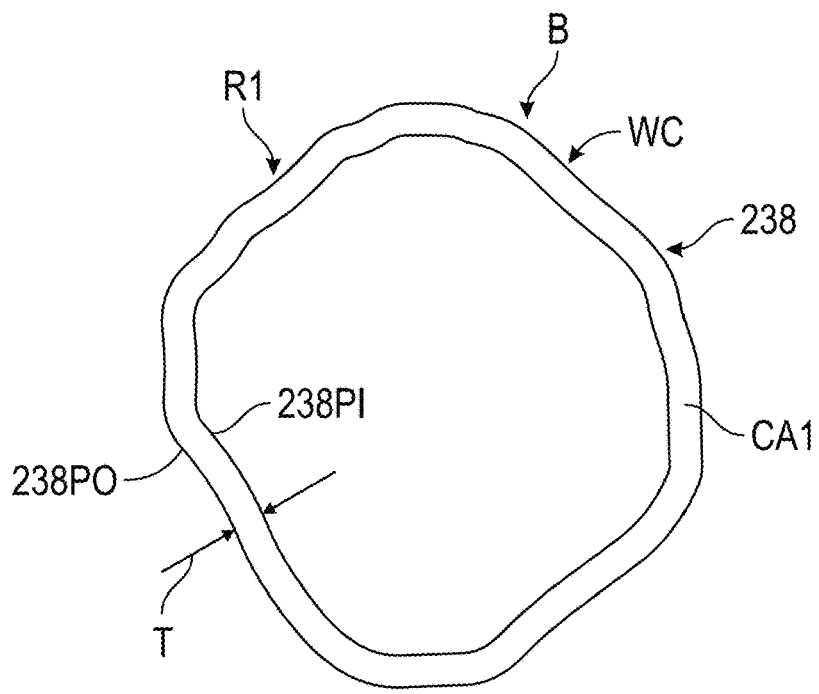
FIGS. 7A-7B illustrate perimeters of exemplary bone models.

In some implementations, the inner perimeter 138PI and/or outer perimeter 138PO of the respective bone model 138 is based on one or more predetermined values. Referring to FIG. 7A, with continuing reference to FIG. 2, a predefined thickness T may be assigned to a bone model 238 during configuration of the system 20 or manually by the surgeon by interaction with the user interface 162. The predefined thickness T may be set based on a statistical analysis of data corresponding to a sample population of one or more prior surgical cases stored in the database 136. For example, an outer perimeter 238PO of a cortical wall WC may be determined utilizing one or more edge detection techniques.

The spatial module 154 may be configured to apply the predefined thickness T to the outer perimeter 238PO to establish an inner perimeter 238PI. The inner perimeter 238PI may follow a contour of the outer perimeter 238PO according to the predefined thickness T and approximates a boundary between the cortical wall WC and the cancellous bone B2 (FIGS. 6A-6B). The predefined thickness T may be stored in the respective surgical plan 142 and may be changed in response to user interaction with the user interface 162 to adjust the inner perimeter 238PI and/or outer perimeter 238PO. The various parameters disclosed herein may be updated in response to a change in predefined thickness T. The surgeon may change a value of the predefined thickness T based on various factors, such as one or more images and other information presented via the user interface 162 and an evaluation of the surgical case.

Figure 7B:
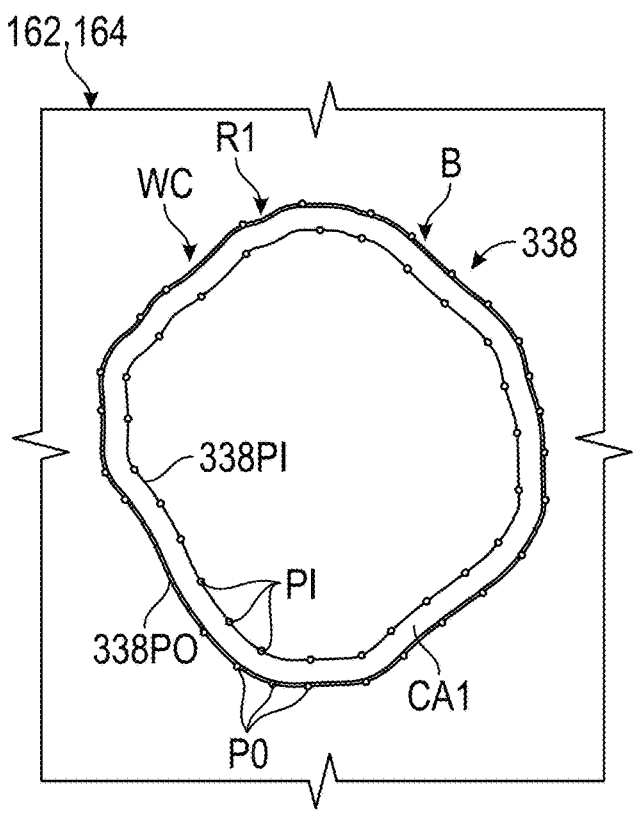

In some implementations, the surgeon may interact with the user interface 162 to approximate the inner and/or outer boundaries of the cortical wall WC. Referring to FIG. 7B, with continuing reference to FIG. 2, the spatial module 154 may be configured to determine an outer perimeter 338PO of a bone model 338 in response to user interaction that defines a first set of points PO adjacent to an outer profile of the cortical wall WC. The spatial module 154 may be configured to determine an inner perimeter 338PI of the bone model 338 in response to user interaction that defines a second set of points PI adjacent to an inner profile of the cortical wall WC.

The surgeon may interact with the one of the display windows 164 of the user interface 162, such as the second display window 164-4 (FIG. 3), to position the sets of points PI and/or PO relative to an image of the bone B. The spatial module 154 may be configured to interconnect the set of points PI and/or PO to establish the inner perimeter 338PI and/or outer perimeter 338PO of the bone model 338. The inner perimeter 338PI and/or outer perimeter 338PO may approximate the inner and/or outer boundaries of the cortical wall WC. Various techniques may be utilized to interconnect the sets of points PI and/or PO, including linear line segments and best-fit techniques utilizing one or more polynomial relationships, for example. The exemplary techniques disclosed herein may be combined to determine the boundaries of the cortical wall WC of a respective bone B.

Referring to FIG. 8, with continuing reference to FIG. 2, the comparison module 156 may be configured to determine one or more relationships between a selected bone model 438 and a selected implant model 440, including a cortical area CA1 and contact area CA2. The cortical area CA1 may be bounded by at least one perimeter. For example, the cortical area CA1 may correspond to an area between an inner perimeter 438PI and outer perimeter 438PO along a first reference plane REF1. The cortical area CA1 may be bounded by the inner perimeter 438PI and outer perimeter 438PO. The first reference plane REF1 may be extend along the resection plane R1. The contact area C2 may correspond to a first region of overlap OR1 between the selected implant model 440 and the cortical area CA1 in which the selected implant model 440 contacts the selected bone model 438 along the first reference plane REF1.

In some implementations, the spatial module 154 may be configured to determine a bone area BA defined as an area surrounded by the outer perimeter 438PO along the first reference plane REF1. The comparison module 156 may be configured to determine a percentage of the contact area CA2 with respect to the bone area BA. The comparison module 156 may be configured to cause the display module 152 to generate at least one indicator in response to the percentage of the contact area CA2 exceeding at least one predefined contact threshold, as illustrated by indicator PI in FIG. 12. The indicator PI may include various states, such as an UP arrow indicating that the predefined contact threshold(s) are met and a DOWN arrow indicating that the predefined contact threshold(s) are not met. Other example indicators may include a color coding status and a value of the percentage of the contact area CA2, as illustrated by indicator PV in FIG. 12.

The comparison module 156 may be configured to update the determined cortical area CA1 and/or contact area CA2 in response to changes in the surgical plan 142, such as selection of a different implant model 440 and changes in a geometry of the selected bone model 438. For example, the comparison module 156 may be configured to update the contact area CA2 in response to relative movement between the selected implant model 440 and the selected bone model 438 along the first reference plane REF1. The surgeon may interact with the user interface 162 to cause the selected implant module 440 to move in a direction DIR1, as illustrated by implant model 440' in FIG. 9. The comparison module 156 may be configured to determine a cortical area CA1' and contact area CA2' associated with the change in position of the implant model 440'. The cortical area CA1' associated with the bone model 438' may be equal to the cortical area CA1 associated with the bone model 438 of FIG. 8, but the contact area CA2' associated with the implant model 440' may differ from the contact area CA2 associated with the implant module 440 due to the change in position.

The comparison module 156 may be configured to determine the contact area CA2 for different resection angles ($\alpha$). For example, the surgeon may interact with the user interface 162 (FIG. 2) to change (e.g., increase or decrease) the resection angle ($\alpha$) to cause a change in orientation of the resection plane R1 associated with the bone model 438 of FIG. 8, as illustrated by modified bone model 538 in FIG. 10. The first reference plane REF1 may be updated in response to the change in the resection angle ($\alpha$).

The spatial module 154 may be configured to adjust a position of the selected implant model 540 relative to the modified bone model 538 in response to the change in resection angle (α), as illustrated in FIG. 10. The comparison module 156 may be configured to determine the cortical area CA1 and contact area CA2 associated with the change in the resection angle (α). The cortical area CA1 associated with the bone model 438 of FIG. 8 may differ from the cortical area CA1 associated with the modified bone model 538 of FIG. 10 due to a profile of the respective bone. Accordingly, the contact area CA2 associated with the bone model 438 may differ from the contact area CA2 associated with the bone model 538 due to the change in the resection angle (α). One would understand how to program the comparison module 156 with logic to determine areas including the cortical area CA1 and contact area CA2.

Figure 11:
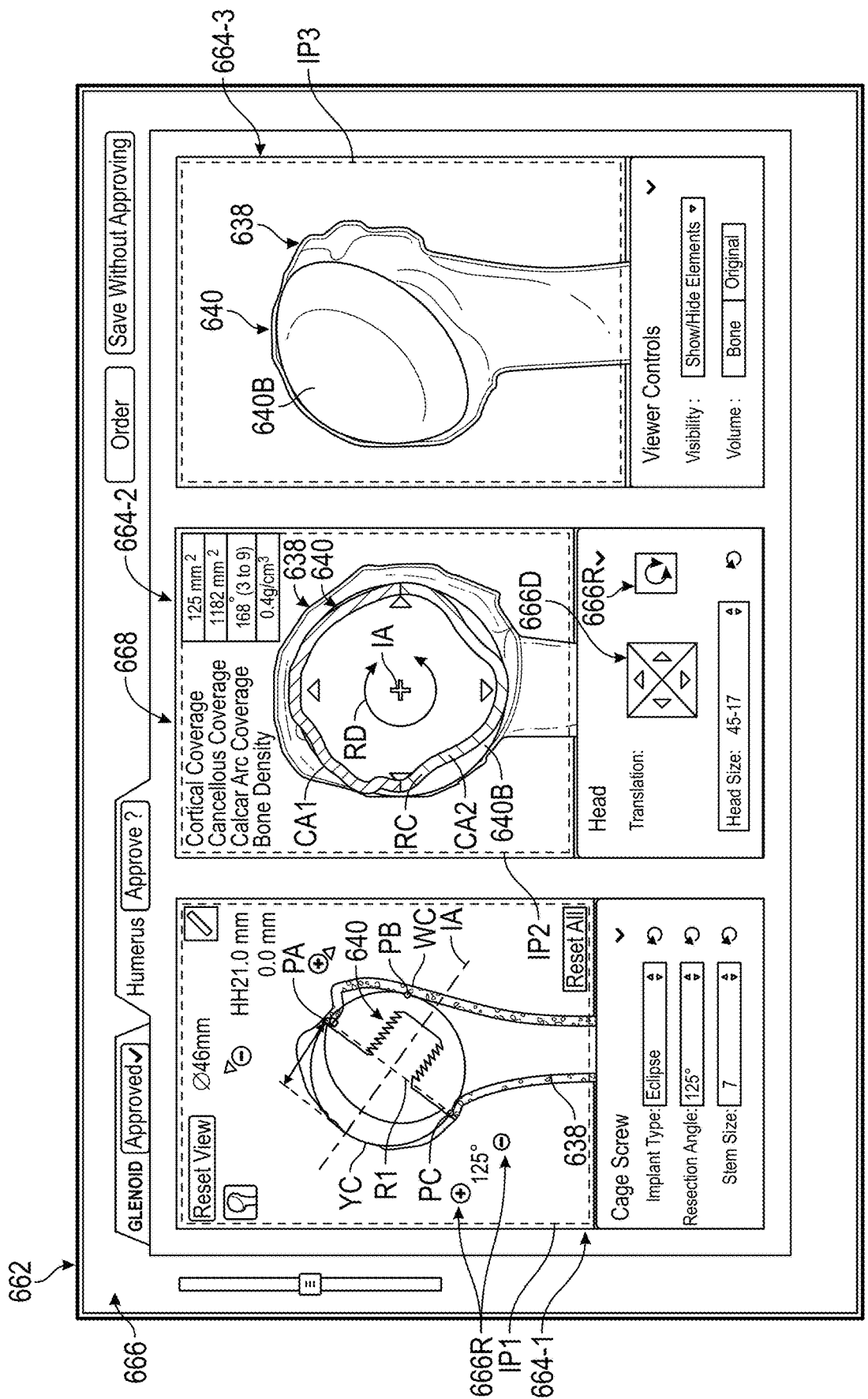

Referring to FIG. 11, with continuing reference to FIG. 2, the comparison module 156 may be configured to cause the display module 152 to display at least one or more indicators relating to a contact area CA2 in a graphical user interface (GUI) 662. The contact area CA2 may be associated with a selected bone model 638 and a selected implant model 640.

Referring to FIG. 12, with continuing reference to FIG. 11, the indicators may include a visual contrast between the contact area CA2 and a remainder of the cortical area CA1 that excludes the contact area CA2. The contact area CA2 may be shown in a different shade and/or color than the remainder of the cortical area CAE The visual contrast is shown as hatching in FIGS. 11-12 for illustrative purposes. The contact area C2 may establish a first region of overlap OR1 between the selected implant model 640 and the cortical area CA1 in which the selected implant model 640 contacts the selected bone model 638 along a first reference plane REF1.

The display module 152 may be configured to cause the user interface 662 to identify different portions of the contact area CA2 using various techniques. The spatial module 154 may be configured to define a calcar region RCAL of the cortical area CAE The calcar region RCAL may extend through a calcar of a bone associated with the selected bone model 638, such as a humerus. The calcar region RCAL may be defined by a calcar arc. The calcar arc may correspond to an arc passing through a point PC. The point PC may be established along a calcar of a humerus, as illustrated in FIG. 11. The calcar arc may be defined by a calcar angle (β). The calcar angle (β) may be a predefined value or may be set by the user through interaction with the user interface 662. The calcar angle (β) may extend less than or equal to approximately 180 degrees along the cortical area CA1 between boundaries BR1, BR2. Each boundary BR1, BR2 may be established with respect to the longitudinal axis A of the bone model 638. In some implementations, the user may set the calcar angle (β) by moving boundary indicators BI1, BI2 in the second display window 664-2 about the longitudinal axis A to set a position of the respective boundaries BR1, BR2. The disclosed techniques may allow the surgeon to vary the calcar region RCAL based on evaluating the bone quality and other conditions of the surgical site, which provides an improvement over prior systems by presenting detailed refinements in the determined contact area CA2 and isolated subregions of interest based on feedback from the surgeon.

Various techniques may be utilized to establish a position of the point PC. The surgeon may interact with the user interface 662 to set a position of one or more points such as points PA, PB, PC to establish an elliptical object YC relative to the bone model 638, as illustrated in FIG. 11. The elliptical object YC may be a "Youderian" circle that characterizes an anatomy of a bone relative to a specified resection plane RE The user may interact with the user interface 662 to establish one or more points along the resection plane R1 include the points PA, PC. The user may interact with the user interface 662 to establish one or more points adjacent the cortical wall WC, such as point PB. The spatial module 154 may be configured to establish and dimension a respective Youderian circle YC along the points PA, PB and/or PC.

The comparison module 156 may be configured to divide the first region of overlap OR1 between two or more sub-regions and cause the display module 152 to display the sub-regions distinctly from each other in the user interface 662. The comparison module 156 may be configured to determine a second region of overlap OR2 between the calcar region RCAL and the first region of overlap OR1. A portion of the first region of overlap OR1 that excludes the second region of overlap OR2 may define a first subregion SR1 of the first region of overlap OR1. The second region of overlap OR2 may define as a second subregion SR2 of the first region of overlap OR1. Various techniques can be utilized to determine the subregions SR1, SR2, including comparing the coordinate spaces of the first region of overlap OR1, second region of overlap OR2 and calcar region RCAL relative to each other to determine overlapping and non-overlapping regions.

The comparison module 156 may be configured to cause the display module 152 to display a first indicator I1 that identifies the first subregion SR1 and a second indicator I2 that identifies the second subregion SR2. In some implementations, the first indicator I1 and second indicator I2 may be textual objects. In other implementations, the first indicator I1 and second indicator I2 may establish visual contrasts between the respective first and second subregions SR1, SR2 and a remainder of the cortical area CA1 that excludes the contact area CA2, as illustrated in FIG. 12. The comparison module 156 may be configured to cause the display module 152 to display a third indicator I3 that identifies the remainder of the cortical area CA1 that excludes the contact area CA2.

The first indicator I1 and second indicator I2 may be displayed in a different shade and/or color than each other and/or the third indicator I3. The visual contrast between indicators I1, I2 is shown as different hatching in FIG. 12 for illustrative purposes. The indicator I3 omits any hatching in FIG. 12 for illustrative purposes. The comparison module 156 may be configured to cause the display module 152 to update the indicators I1, I2, I3 in response to change(s) relating to the selected bone model 638 and/or selected implant model 640, such as movement of implant model 640' as illustrated by indicators I1', I2', I3' in FIG. 13. The disclosed techniques, including separately identifying the subregions SR1, SR2 of the contact area CA2, provides an improvement over prior systems by conveying an enhanced representation of a relationship of the contact area CA2 with respect to the cortical area CA1 of the respective bone B and selected resection parameters. The surgeon may interact with the user interface 162 to tailor the surgeon plan 142 in an iterative manner based on this enhanced representation, which may improve efficiency in pre-operative planning, reduce inter-operative time that may otherwise be caused by changes to the surgical plan, and improve the surgical outcome for the patient based on a selection of parameters that more closely aligns with a relationship between the selected implant and an anatomy of the patient including bone quality and geometry along a resected surface.

The comparison module 156 may be configured to cause the display module 152 to display one or more parameters associated with the contact area CA2 in a graphic 668. The graphic 668 may overlay or be arranged adjacent to the second display window 664-2 of the user interface 662, for example. Example parameters include a cortical coverage parameter 668A, cancellous coverage parameter 668B, calcar arc coverage parameter 668C, bone density parameter 668D and/or weighted contact area parameter 668E.

The cortical coverage parameter 668A may be defined as a value of the contact area CA2 between the inner perimeter 638PI and outer perimeter 638PO along the resection plane R1 and may be indicative of a portion of an implant associated with the selected implant model 640 that may be supported by cortical bone along the cortical wall WC.

The cancellous coverage parameter 668B may be defined as a value of the contact area CA2 surrounded by the inner perimeter 638PI and may be indicative of a portion of an implant associated with the selected implant model 640 that may be supported by the cancellous bone. The cortical coverage parameter 668A and cancellous coverage parameter 668B may be expressed in units of cm^2, for example.

The calcar arc coverage parameter 668C may be defined as a portion of the calcar angle ($\beta$) of the calcar arc in which the contact area CA2 is established along the calcar region RCAL. The value may be less than or equal to the calcar angle ($\beta$) of the calcar arc.

The bone density parameter 668D may be defined as an average density of the respective bone along the contact area CA2, which may be expressed in units of gram/cm^3, for example. Various techniques may be utilized to determine or approximate the bone density parameter 668D. For example, a first predefined density value may be defined for cortical bone, and a second, different predefined density value may be defined for cancellous bone. The calcar region CR may comprise relatively more dense/strong bone tissue than other portions of the cortical wall. In some implementations, the second region of overlap OR2 associated with the calcar region CR may be assigned a different (e.g. greater) predefined density value than a predefined density value associated with a remainder of the contact area CA2 along the cortical wall WC. Each bone model 138 may include one or more predefined bone density values associated with or assigned to respective portions of a volume of the bone model 138. For example, each coordinate of the bone model 138 may be assigned a respective bone density value. The bone density values may be the same or may differ for the volume of the bone model 138. The comparison module 156 may be configured to calculate the bone density parameter 668D based on a product of an area of the second region of overlap OR2 and the respective predefined density value.

Various techniques can be utilized to determine the weighted contact area parameter 668E. In some implementations, the spatial module 154 is configured to determine a cancellous area of the selected bone model 638. The cancellous area may correspond to an area of cancellous bone B2 (FIG. 6A) along the first reference plane REF1 that is surrounded by the inner perimeter 638PI, as illustrated by the cancellous region CR. The first region of overlap OR1 corresponding to the contact area CA2 may be assigned or otherwise associated with a first weight. The second region of overlap OR2 between the contact area CA2 and calcar region RCAL may be assigned or otherwise associated with a second weight. The cancellous area corresponding to the cancellous region CR may be assigned or otherwise associated with a third weight. The first weight may be greater than the third weight but may be less than the second weight. For example, the second weight may be assigned a multiple of 1.5, the first weight may be assigned a multiple of 1, and the third weight may be assigned a multiple of 0.5. The comparison module 156 may be configured to determine a value of the weighted contact area parameter 668E associated with the contact area CA2 according to the first, second and third weights. The comparison module 156 may be configure to determine a value of the bone density parameter 668D based on the value of the weighted contact area parameter 668E.

The comparison module 156 may be configured to update the parameters 668A-668E in response to changes relating to the selected bone model 638 and/or selected implant model 640. For example, the comparison module 156 may be configured to update the parameters 668A-668E in response movement of the selected implant model 640, as illustrated by parameters 668A'-668E' in FIG. 13.

The comparison module 156 may be configured to cause the display module 152 to display one or more indicators I3-I7 associated with the parameters in the graphic 668. For example, each indicator I3-I7 may include a color-coded box based a predefined threshold associated with the respective parameter 668A-668E. Each color-coded box may include one or more states. For example, a first color (e.g., green) may indicate that a value of the respective parameter 668A-668E meets the predefined threshold, and a second color (e.g., red) may indicate that the value of the respective parameter 668A-668E does not meet the predefined threshold. The comparison module 156 may be configured to cause the display module 152 to change the state of one or more of the indicators I3-I7 in response to the changes relating to the selected bone model 638 and/or selected implant model 640.

The surgeon may evaluate the indicators I3-I7 and values of the various parameters 668A-668E to revise the respective surgical plan 142 (FIG. 2). For example, the surgeon may evaluate a quality of the bone including the value of the bone density parameter 668D to values of the cortical coverage parameter 668A, cancellous coverage parameter 668B, calcar arc coverage parameter 668C and/or weighted contact area parameter 668E. The surgeon may determine that a desired value of the bone density parameter 668D may or may not be suitable for a particular patient, even though a value of the surface area of the bone along the reference plane REF1 and/or a value of the contact area CA2 may be sufficient. The surgeon may interact with the user interface 662 to approach or meet the desired value of the bone density parameter 668D, such as changing the specified resection angle ($\alpha$) and/or resection plane R1, moving the selected implant model 640 relative to the resection plane R1, and/or selected another implant model 140 from the database 136 (FIG. 2). For example, the surgeon may decrease the resection angle ($\alpha$) to provide relatively more support to the selected implant model 140. The surgeon may approve a surgical plan 142 having a value of the cortical coverage parameter 668A that exceeds a predefined threshold, even though a value of the cancellous coverage parameter 668B is below another predefined threshold, for example. The techniques disclosed herein may therefore provide the surgeon with an additional number of options in implant and surgical technique selection to improve the surgical outcome.

The user interface 662 may include at least one button 666BR (FIG. 12) that may be selected to present literature to the surgeon in assisting the surgeon in making the various selections and modifications to the surgical plan 142. The literature may include a relative portion of a user manual explaining aspects of the indicators I1-7 and respective parameters 668A-668E and techniques for causing changes in the respective values to achieve a desired outcome. The literature presented to the user in response to selection of the button 666BR may be based on values of the parameters 668A-668E meeting various criteria, such as being below (or above) predetermined thresholds.

Figure 14:
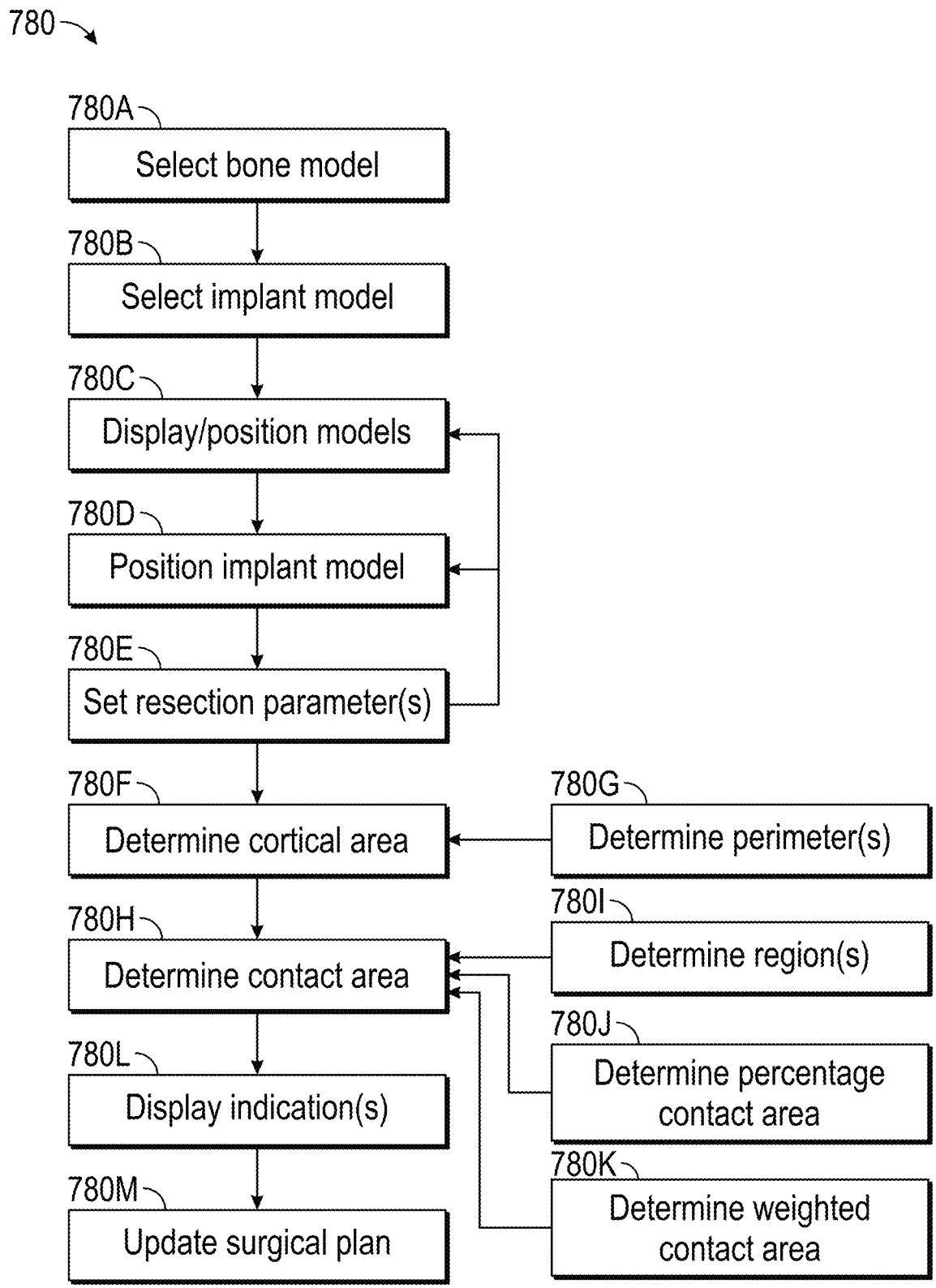
FIG. 14 illustrates an exemplary method of planning an orthopaedic procedure.

FIG. 14 illustrates an exemplary method of planning an orthopaedic procedure in a flowchart 780. The method may be utilized pre-operatively, intra-operatively and/or post-operatively to create, edit, execute and/or review a respective surgical plan. The method may be utilized to perform an arthroplasty for restoring functionality to shoulders and other joints. Although the method 780 primarily refers to implants for repair of a defect in a humerus during a shoulder reconstruction, it should be understood that the method and disclosed implants may be utilized in other locations of the patient and other surgical procedures, such as the glenoid or any other location disclosed herein. The method 780 can be utilized with any of the planning systems disclosed herein. Fewer or additional steps than are recited below could be performed within the scope of this disclosure, and the recited order of steps is not intended to limit this disclosure. Reference is made to the planning systems 120, 620 for illustrative purposes.

Referring to FIGS. 2-3, with continuing reference to FIG. 14, a bone model(s) 138 may be selected from one or more bone models 138 by interacting with a graphical user interface 162 at step 780A. An implant model 140 may be selected from one or more implant models 140 by interacting with the user interface 162 at step 780B. Available bone models 138 and implant models 140 in the database(s) 136 may be presented in one or more lists in the user interface 162 that may be selected in response to user interaction, for example. The selected bone model 138 may correspond to a bone associated with a joint, such as a humeral head of a humerus as illustrated in FIG. 3.

Referring to FIGS. 11 and 12, with continuing reference to FIG. 14, a selected one of the one or more implant models 640 and a selected one of the one or more bone models 638 may be initially positioned and displayed in one or more windows 664 of the user interface 662 at step 780C. Each selected bone model 638 and selected implant model 640 may be displayed in the display windows 664-1, 664-2 and 664-3 according to any of the techniques disclosed herein, including different orientations and 2D/3D views. Each selected bone model 638 and selected implant model 640 may be displayed in the display window 664-2 relative to the viewing plane IP2.

The selected implant model 640 may be positioned relative to the selected bone model 638 at step 780D. For example, the selected implant model 640 may be moved from the position illustrated in FIG. 12 to a position of the selected implant model 640' in FIG. 13. A position of the selected implant model 640 may be adjusted in one or more iterations and prior to, during and/or subsequent to any of the steps of method 780.

One or more resection parameters may be set at step 780E. The resection parameters may include a resection angle (α) and/or resection plane R1 associated with the resection angle (α) (see FIG. 4). The resection parameters may be stored in the respective surgical plan 142 (FIG. 2). Step 780E may include selecting a resection angle (α) to define a resection plane R1 along the selected bone model 638. Step 780E may include setting the first reference plane REF1 to be coincident with the resection plane R1. Step 780E may include setting the image IP2 plane of the respective window 664-2 to be parallel to the resection plane R1, as illustrated in FIG. 12.

Step 780E may include setting the first image plane IP1 of the first display window 664-1 to be perpendicular to the second image plane IP2 of the second display window 664-2, as illustrated by FIG. 11. Step 780C and/or step 780D may include positioning the selected implant model 640 along the resection plane R1 such that a volume of the selected implant model 640 is partially received in a volume of the selected bone model 638, as illustrated in FIG. 11.

At step 780F a cortical area CA1 associated with the selected bone model 638 may be determined. The cortical area CA1 may be determined utilizing any of the techniques disclosed herein. For example, step 780F may include determining one or more perimeters at step 780G. Step 780G may include determining the inner perimeter 638PI and/or outer perimeter 638PO along the first reference plane REF1, which may correspond to the resection plane R1. Step 780F may include updating the determined cortical area CA1 in response to changing the selected resection angle (α) and/or changing a shape of the bone model 638 along the resection plane R1 such as by defining one or more recesses in the resection face.

At step 780H a contact area CA2 is determined between the selected bone model 638 and the selected implant model 640 along a specified portion of the selected bone model 638, such as along the reference plane REF1. The contact area CA2 may be determined utilizing any of the techniques disclosed herein. Step 780H may include determining one or more regions of overlap associated with the contact area CA2 at step 780I. Step 780I may include determining the first region of overlap OR1 corresponding to the contact area CA2 and/or determining a second region of overlap OR2 between the contact area CA2 and a calcar region RCAL of the cortical area CAL as illustrated in FIG. 12.

Step 780H may include updating the contact area CA2 in response to moving the selected implant model 640 relative to the selected bone model 638, as illustrated by the implant model 640' of FIG. 13. Step 780H may include updating the determined contact area CA2 in response to changing the selected resection angle (α).

A percentage contact area may be determined at step 780J. Referring to FIG. 8, with continuing reference to FIG. 14, step 780J may include determining the bone area BA and determining a percentage of the contact area CA2 with respect to the bone area BA.

Step 780H may include determining a weighted value of the contact area CA2 at step 780K. The weighted value of the contact area CA2 can be determined utilizing any of the techniques disclosed herein. Step 780K may include determining a bone density of the selected bone model 638 along the contact area CA2 based on the weighted value of the contact area CA2.

At step 780L, at least one or more indicators relating to the contact area CA2 may be displayed in the display window(s) 664 and/or another portion of the user interface 662, such as the display window 664-2 relative to the image plane IP2. Step 780L may include displaying any of the indicators and parameters disclosed herein, including the indicators I1-I7, PI, PV and parameters 668A-668E of FIG. 12.

Step 780L may include displaying a perimeter of the second region of overlap OR2 along the calcar region RCAL in the display window 664-2 as illustrated by indicator I1, displaying a perimeter of a remainder of the contact area CA in the display window 664-2 that excludes the second region of overlap OR2 as illustrated by indicator I2, and/or displaying a perimeter of a remainder of the cortical area CA1 in the display window 664-2 that excludes the contact area CA2, as illustrated by indicator I3 in FIG. 12. The remainder of the cortical area CA1 that excludes the contact area CA2 may be a single contiguous region or two or more separate regions based on a placement of the selected implant model 640.

Step 780L may include displaying the percentage of the contact area CA2 determined at step 780J in the user interface 662. Step 780L may include displaying a first indicator in response to the percentage of the contact area CA2 meeting at least one predefined contact threshold, but displaying the second indicator in response to the percentage of the contact area CA2 being below the at least one predefined contact threshold. The first and second indicators may correspond to different stages of the percentage indicator PI of FIGS. 12-13, for example. Step 780L may include displaying a numerical value of the percentage of the contact area CA2, as illustrated by indicator PV of FIG. 12.

Step 780L may include displaying a value of the weighted contact area parameter 668E in the user interface 662 that is determined in step 780K, as illustrated in FIG. 12. Step 780L may include displaying an indicator in the user interface 662 in response to the weighted contact area exceeding at least one predefined weighted contact threshold, but displaying another indicator in the user interface 662 in response to the weighted contact area being below the at least one predefined weighted contact threshold. The indicator may be different states of the indicator 17 associated with the weighted contact area parameter 668E, and may include any of the status techniques disclosed herein.

The surgeon may perform one or more steps in response to a status or value of any of the parameters disclosed herein, including the parameters 668A-668E and indicators I1-I7, PI, PV, such as a value of the weighted contact area being below the predefined weighted contact threshold(s). For example, the surgeon may select another one of the implant models 140 stored in the database(s) 136 (FIG. 2). The surgeon may change the selected resection angle (α) at step 780E. The surgeon may interact with the user interface 662 to move the selected implant model 640 along the resection plane RE In some implementations, the selected implant model 640 may have a non-circular outer perimeter 640PO. The surgeon may interact with the user interface 662, such as a button 666R in the second window 664-2, to rotate the selected implant model 640 in a direction RD about an implant axis IA that extends through the resection plane R1, as illustrated in FIG. 11.

Step 780L may include displaying one or more indicators in the user interface 662 in response to a value of the bone density parameter 668D exceeding at least one predefined density threshold, but displaying another indicator in the user interface 662 in response to the value of the bone density being below the at least one predefined density threshold. The indicator may be different states of the indicator 16 associated with the bone density parameter 668D, and may include any of the status techniques disclosed herein. The value of the bone density parameter 668D may be based on the weighted value of the contact area determined at step 780K.

Referring to FIG. 2, with continuing reference to FIG. 14, the surgical plan 142 may be updated at step 780M. Step 780M may include updating a local instance of the surgical plan 142 and/or updating the surgical plan 142 in the database 136. One or more iterations of the step(s) of the method 780 may be performed to update the surgical plan 142.

The novel planning systems and methods of this disclosure can be incorporated to a practical application by providing improved positioning of implants relative to a bone surface, such as a resected face of a bone, based on conveying an enhanced representation of implant contact area relative to the cortical wall and other portions of the respective bone. The planning systems and methods may be utilized to more quickly and efficiently establish a surgical plan that reduces intra-operative time and increases precision and reproducibility of an implant position through pre-operative planning consideration of specific information relating to the relationship between the implant and an anatomy of the patient. The selected implant may be viewed substantially normal to a resection surface, which may provide the surgeon a better understanding of a shape of the osteotomy, surface area contact and amount of support and fixation for the selected implant. The planning systems may include various indicators to provide feedback to the surgeon regarding a selected implant and surgical site preparation based on surface area coverage, bone quality and bone density, for example, which can improve implant stability and healing of the patient by more closely tailoring the surgical plan to the specific patient.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A system for planning an orthopaedic procedure comprising:
    a computing device including a processor coupled to a memory, wherein the processor is configured to execute a planning environment including a display module, a spatial module and a comparison module;
    wherein the memory is configured to store one or more implant models and one or more bone models;
    wherein the spatial module is configured to establish an outer perimeter and an inner perimeter along a first reference plane, and the inner and outer perimeters are associated with respective inner and outer profiles of a cortical wall of the selected bone model;
    wherein the display module is configured to display in a first display window of a graphical user interface a selected one of the implant models and a selected one of the bone models relative to a first image plane;
    wherein the comparison module is configured to determine a value of a cortical area and a value of a contact area, the cortical area corresponds to an area between the inner perimeter and the outer perimeter along the first reference plane, and the contact area corresponds to a first region of overlap between the selected implant model and the cortical area in which the selected implant model contacts the selected bone model along the first reference plane; and wherein the comparison module is configured to cause the display model to display at least one indicator relating to the value of the contact area in the graphical user interface.

2. The system as recited in claim 1, wherein the comparison module is configured to update the contact area in response to relative movement between the selected implant model and the selected bone model along the first reference plane.

3. The system as recited in claim 1, wherein the display module is configured to set the first image plane to be parallel to the first reference plane.

4. The system as recited in claim 1, wherein the at least one indicator includes a visual contrast between the contact area and a remainder of the cortical area that excludes the contact area.

5. The system as recited in claim 1, wherein:
the spatial module is configured to determine a bone area defined as an area surrounded by the outer perimeter along the first reference plane;
the comparison module is configured to determine a percentage of the contact area with respect to the bone area; and
the at least one indicator is generated in response to the percentage of the contact area exceeding at least one predefined contact threshold.

6. The system as recited in claim 1, wherein the spatial module is configured to establish a resection plane along the selected bone model, the resection plane is defined by a resection angle, the display module is configured to set the first reference plane to be coincident with the resection plane, and the display module is configured to set the first image plane to be parallel to the resection plane.

7. The system as recited in claim 6, wherein a volume of the selected implant model is partially received in a volume of the selected bone model along the resection plane.

8. The system as recited in claim 6, wherein the comparison module is configured to update the cortical area and the contact area in response to a change in the resection angle.

9. The system as recited in claim 6, wherein the graphical user interface includes a second display window, the display module is configured to display in the second display window the selected implant model and the selected bone model relative to a second image plane, and the second image plane is transverse to the first image plane.

10. The system as recited in claim 6, wherein the display module is configured to graphically depict an entirety of the contact area along the first image plane.

11. The system as recited in claim 10, wherein:
the value of the contact area is a weighted value including a first weight and a second weight, the first weight is associated with the first region of overlap, the second weight is associated with a region of overlap between the selected implant model and a cancellous area of the selected bone model, and the cancellous area corresponds to an area along the first reference plane that is surrounded by the inner perimeter.

12. The system as recited in claim 1, wherein the spatial module is configured to define a calcar region of the cortical area, the calcar region extends through a calcar of a bone associated with the selected bone model, the comparison module is configured to determine a second region of overlap between the calcar region and the first region of overlap, the at least one indicator includes a first indicator that identifies a portion of the first region of overlap that excludes the second region of overlap, and the at least one indicator includes a second indicator that identifies the second region of overlap.

13. The system as recited in claim 12, wherein the first indicator and the second indicator establish visual contrasts between each other and a remainder of the cortical area that excludes the contact area.

14. The system as recited in claim 1, wherein the spatial module is configured to determine the outer perimeter in response to user interaction that defines a first set of points adjacent to the outer profile of the cortical wall, and the spatial module is configured to determine the inner perimeter in response to user interaction that defines a second set of points adjacent to the inner profile of the cortical wall.

15. The system as recited in claim 1, wherein the selected bone model corresponds to a bone associated with a joint.

16. A method of planning an orthopaedic procedure comprising:
selecting a bone model from a plurality of bone models by interacting with a graphical user interface;
selecting an implant model from a plurality of implant models by interacting with the graphical user interface;
displaying in a first display window of a graphical user interface a selected one of the implant models and a selected one of the bone models relative to a first image plane;
determining an outer perimeter and an inner perimeter along a first reference plane, wherein the inner and outer perimeters are respectively associated with inner and outer profiles of a cortical wall of the selected bone model;
determining a value of a cortical area and a value of a contact area, wherein the cortical area corresponds to an area between the inner perimeter and the outer perimeter along the first reference plane, and the contact area corresponds to a first region of overlap between the selected implant model and the cortical area in which the selected implant model contacts the selected bone model along the first reference plane; and
displaying in the first display window at least one indicator relating to the value of the contact area.

17. The method as recited in claim 16, further comprising:
updating the contact area in response to moving the selected implant model relative to the selected bone model.

18. The method as recited in claim 16, further comprising:
selecting a resection angle to define a resection plane along the selected bone model;
setting the first reference plane to be coincident with the resection plane; and
setting the first image plane to be parallel to the resection plane.

19. The method as recited in claim 18, further comprising:
displaying in a second display window of the graphical user interface the selected implant model and the selected bone model relative to a second image plane, the second image plane being transverse to the first image plane.

20. The method as recited in claim 19, further comprising:
setting the second image plane to be perpendicular to the first image plane; and
positioning the selected implant model along the resection plane such that a volume of the selected implant model is partially received in a volume of the selected bone model.

21. The method as recited in claim 18, further comprising:
updating the determined cortical area and the determined contact area in response to changing the selected resection angle.

22. The method as recited in claim 18, further comprising:
determining a bone area, wherein the bone area is defined as an area surrounded by the outer perimeter along the first reference plane;
determining a percentage of the contact area with respect to the bone area;
displaying the percentage of the contact area in the graphical user interface;
wherein the at least one indicator includes a first indicator and a second indicator; and
displaying the first indicator in response to the percentage of the contact area meeting at least one predefined contact threshold, but displaying the second indicator in response to the percentage of the contact area being below the at least one predefined contact threshold.

23. The method as recited in claim 18, further comprising:
determining a second region of overlap between the contact area and a calcar region of the cortical area, wherein the calcar region extends through a calcar of a bone associated with the selected bone model;
displaying a perimeter of the second region of overlap in the first display window;
displaying a perimeter of a remainder of the contact area in the first display window that excludes the second region of overlap; and
displaying a perimeter of a remainder of the cortical area in the first display window that excludes the contact area.

24. The method as recited in claim 23, wherein the at least one indicator includes a first indicator and a second indicator, and further comprising:
determining a cancellous area of the selected bone model, the cancellous area corresponding to an area along the first reference plane that is surrounded by the inner perimeter;
wherein the first region of overlap is associated with a first weight, the second region of overlap is associated with a second weight, the cancellous area is associated with a third weight, and wherein the first weight is greater than the third weight but is less than the second weight;
wherein the step of determining the value of the contact area includes determining a weighted value of the contact area according to the first, second and third weights; and
displaying the first indicator in the graphical user interface in response to the weighted contact area exceeding at least one predefined weighted contact threshold, but displaying the second indicator in the graphical user interface in response to the weighted contact area being below the at least one predefined weighted contact threshold.

25. The method as recited in claim 24, wherein the at least one indicator includes a third indicator and a fourth indicator, and further comprising:
determining a bone density of the selected bone model along the contact area based on the weighted value of the contact area; and
displaying the third indicator in the graphical user interface in response to the bone density exceeding at least one predefined density threshold, but displaying the fourth indicator in the graphical user interface in response to the bone density being below the at least one predefined density threshold.

26. The method as recited in claim 24, further comprising:
selecting a resection angle to define a resection plane along the selected bone model;
setting the first reference plane to be coincident with the resection plane;
setting the first image plane to be parallel to the resection plane;
performing at least one of the following steps in response to the weighted contact area being below the at least one predefined weighted contact threshold:
selecting another implant model from the plurality of implant models; changing the selected resection angle; moving the selected implant model along the resection plane; and/or rotating the selected implant model about an implant axis that extends through the resection plane.

27. The method as recited in claim 18, wherein the selected bone model corresponds to a bone associated with a joint.

28. The method as recited in claim 27, wherein the bone is a humeral head of a humerus.

29. A system for planning an orthopaedic procedure comprising:
a computing device including a processor coupled to a memory, wherein the processor is configured to execute a planning environment including a display module, a spatial module and a comparison module;
wherein the memory is configured to store an implant model and a bone model;
wherein the spatial module is configured to establish a perimeter along a reference plane, and the perimeter is associated with a profile of a cortical wall of the bone model;
wherein the display module is configured to display in a display window of a graphical user interface the implant model and the bone model relative to an image plane; and
wherein the comparison module is configured to determine a value of a cortical area and a value of a contact area, the cortical area bounded by the perimeter, and the contact area corresponding to a region of overlap between the implant model and a cortical area in which the implant model contacts the bone model along the reference plane.

30. The system as recited in claim 29, wherein the comparison module is configured to cause the display model to display an indicator relating to the value of the contact area in the graphical user interface.

* * * * *